United States Patent
Kawakami et al.

(10) Patent No.: US 11,382,870 B2
(45) Date of Patent: Jul. 12, 2022

(54) RISPERIDONE-CONTAINING PATCH

(71) Applicant: TEIKOKU SEIYAKU CO., LTD., Kagawa (JP)

(72) Inventors: Satoshi Kawakami, Sanuki (JP); Manabu Sogabe, Awa (JP); Taiki Shibata, Higashikagawa (JP); Hiroaki Hasegawa, Ibaraki (JP)

(73) Assignee: TEIKOKU SEIYAKU CO., LTD., Kagawa (JP)

( * ) Notice: Subject to any disclaimer, the term of this patent is extended or adjusted under 35 U.S.C. 154(b) by 173 days.

(21) Appl. No.: 16/500,446

(22) PCT Filed: Apr. 4, 2018

(86) PCT No.: PCT/JP2018/014412
§ 371 (c)(1),
(2) Date: Oct. 3, 2019

(87) PCT Pub. No.: WO2018/186441
PCT Pub. Date: Oct. 11, 2018

(65) Prior Publication Data
US 2020/0108024 A1    Apr. 9, 2020

(30) Foreign Application Priority Data

Apr. 5, 2017 (JP) .............................. JP2017-075358
Dec. 28, 2017 (JP) .............................. JP2017-253439

(51) Int. Cl.
| | |
|---|---|
| A61K 9/70 | (2006.01) |
| A61K 47/32 | (2006.01) |
| A61K 47/12 | (2006.01) |
| A61P 25/18 | (2006.01) |
| A61K 47/14 | (2017.01) |
| A61K 31/194 | (2006.01) |
| A61K 31/20 | (2006.01) |
| A61K 31/519 | (2006.01) |

(52) U.S. Cl.
CPC .......... A61K 9/7069 (2013.01); A61K 9/7061 (2013.01); A61K 31/194 (2013.01); A61K 31/20 (2013.01); A61K 31/519 (2013.01); A61K 47/32 (2013.01); A61K 47/12 (2013.01); A61K 47/14 (2013.01); A61P 25/18 (2018.01)

(58) Field of Classification Search
None
See application file for complete search history.

(56) References Cited

U.S. PATENT DOCUMENTS

| | | |
|---|---|---|
| 2005/0214529 A1 | 9/2005 | Hasegawa et al. |
| 2006/0110434 A1 | 5/2006 | Yamaguchi et al. |
| 2011/0189261 A1 | 8/2011 | Kuribayashi et al. |
| 2012/0052112 A1* | 3/2012 | Kuribayashi ........ A61K 9/7023 424/449 |

FOREIGN PATENT DOCUMENTS

| | | |
|---|---|---|
| JP | 2006-169238 | 6/2006 |
| JP | 4916200 | 11/2006 |
| JP | 4603398 | 10/2010 |
| JP | 4916200 B2 * | 4/2012 |
| JP | 2014-105205 | 6/2014 |
| WO | 2009/110351 | 9/2009 |
| WO | 2010/098261 | 9/2010 |

OTHER PUBLICATIONS

International Search Report dated Jun. 26, 2018 in International (PCT) Application No. PCT/JP2018/014412.
International Preliminary Report on Patentability dated Oct. 8, 2019 in International (PCT) Application No. PCT/JP2018/014412.

* cited by examiner

*Primary Examiner* — H. Sarah Park
(74) *Attorney, Agent, or Firm* — Wenderoth, Lind & Ponack, L.L.P.

(57) ABSTRACT

The present invention provides a risperidone-containing patch having an excellent drug release property and patch physical properties. Specifically, the present invention provides a medical patch comprising an adhesive composition comprising risperidone or a pharmaceutically acceptable salt thereof; a carboxylic acid; a fatty acid ester; and an adhesive, characterized in that said adhesive is a star-shaped acrylic block polymer having a star-shaped structure in which at least three chain polymer portions radiate from a sulfur residue of a mercapto group situated at the center, wherein the (meth)acrylic acid alkyl ester structural units having 7-17 carbon atoms account for 30-99.99% by mass of the whole structural units in said star-shaped acrylic block polymer, and at least one of said chain polymer portions has a structural unit having a copolymer structure of polymerizable monomers comprising a (meth)acrylic acid alkyl ester having 7-17 carbon atoms and a polyfunctional monomer.

15 Claims, 2 Drawing Sheets

RISPERIDONE-CONTAINING PATCH

TECHNICAL FIELD

The present invention relates to a risperidone-containing patch using a star-shaped acrylic block polymer as an adhesive.

BACKGROUND ART

Risperidone is an atypical antipsychotic belonging to serotonin-dopamine antagonists, and mainly used as a therapeutic agent of a psychiatric disorder such as schizophrenia, mania, and autism by acting on brain centers and blocking serotonin 5-HT2 receptors and dopamine D2 receptors.

Many oral formulations such as tablets and liquids are mainly developed as dosage forms of risperidone formulations. In case of oral formulations, however, the drug may be metabolized by a first-pass effect in intestinal tract and liver etc., and side effects such as anorexia, vomiting, and constipation have been frequently reported. Thus, risperidone-containing patches have recently been developed as formulations which can avoid the drug metabolism caused by a first-pass effect, decrease the side effects, and continuously administer the drug over a long period of time (Patent Documents 1-3).

Meanwhile, in order to prepare a patch which has a continuous and excellent drug release property of risperidone, a high concentration of drug is contained in the patch, and liquid components such as acids and fatty acid esters for improving the solubility and transdermal absorbability of risperidone are contained in the patch. However, when a certain amount of these liquid components is contained in the formulation, conventional rubber adhesives and acrylic adhesives cannot maintain the patch physical properties, and result in problems such as poor cohesive force immediately after the preparation and exudation of the liquid components during the long storage.

Also, risperidone is a poorly-soluble drug. Thus, when a high concentration of risperidone is contained in a patch, a crystal of risperidone may precipitate with lapse of time even if it was completely dissolved therein immediately after the preparation. The crystal precipitation of drug would result in problems such as deteriorated adhesive property of patch and decreased drug permeability.

The above Patent Documents 1 and 2 use conventional rubber adhesives and acrylic adhesives, and thus do not solve the above problems caused by liquid components. Also, the Patent Document 3 uses an acrylic adhesive and a cross-linking agent having an isocyanate group in order to solve the problem caused by liquid components. However, the Patent Document 3 has problems for example in that an acid used for improving the solubility and transdermal absorbability of risperidone inhibits the cross-linking, which makes the sufficient physical properties difficult to be maintained, and that the isocyanate group would affect the stability of risperidone. Further, the Patent Documents 1-3 do not disclose the crystal precipitate of risperidone, and do not evaluate the crystal precipitate with lapse of time.

CITATION LIST

Patent Document

[Patent Document 1] WO 2010/098261 A1
[Patent Document 2] JP 2006-169238 A
[Patent Document 3] JP 2014-105205 A

SUMMARY OF INVENTION

Technical Problem

The present invention has been made to solve the above-mentioned conventional problems. An object of the present invention is to provide a risperidone-containing patch having an excellent drug release property and patch physical properties.

Solution to Problem

The present inventors have earnestly studied to solve the above problems, and found that a patch, which shows an excellent drug release from the formulation and excellent patch physical properties such as having a high cohesive force and causing no exudation of liquid components and no crystal precipitation of the drug etc. during long storage even if liquid components such as carboxylic acids and fatty acid esters are added thereto at a relatively large amount, and being able to be applied to a skin over a long period of time, can be obtained by using a specific star-shaped acrylic block polymer as an adhesive in a risperidone-containing patch, and finally completed the present invention.

Namely, the aspects of the present invention are as follows.

1. Medical Patches, Uses Thereof, and Production Methods Thereof

[1] A medical patch comprising an adhesive composition comprising
  risperidone or a pharmaceutically acceptable salt thereof;
  a carboxylic acid;
  a fatty acid ester; and
  an adhesive
characterized in that said adhesive is a star-shaped acrylic block polymer having a star-shaped structure in which at least three chain polymer portions radiate from a sulfur residue of a mercapto group situated at the center, wherein the (meth)acrylic acid alkyl ester structural units having 7-17 carbon atoms account for 30-99.99% by mass of the whole structural units in said star-shaped acrylic block polymer, and at least one of said chain polymer portions has a structural unit having a copolymer structure of polymerizable monomers comprising a (meth)acrylic acid alkyl ester having 7-17 carbon atoms and a polyfunctional monomer;
[2] The medical patch according to the above [1], wherein the content of the polyfunctional monomer relative to the whole structural units of the star-shaped acrylic block polymer is 0.001-1% by mass;
[3] The medical patch according to the above [1] or [2], wherein the chain polymer portion comprises a polymeric structure of radical polymerizable monomers;
[4] The medical patch according to any one of the above [1]-[3], wherein the (meth)acrylic acid alkyl ester having 7-17 carbon atoms is one or a combination of two or more selected from the group consisting of (meth)acrylic acid butyl ester, (meth)acrylic acid t-butyl ester, (meth)acrylic acid pentyl ester, (meth)acrylic acid hexyl ester, (meth)acrylic acid heptyl ester, (meth)acrylic acid octyl ester, (meth)acrylic acid isooctyl ester, (meth)acrylic acid nonyl ester, (meth)acrylic acid isononyl ester, (meth)acrylic acid decyl ester, (meth)acrylic acid undecyl ester, (meth)acrylic acid dodecyl ester, and (meth)acrylic acid 2-ethylhexyl ester;

[5] The medical patch according to any one of the above [1]-[4], wherein the polyfunctional monomer is one or a combination of two or more selected from bifunctional (meth)acrylates;

[6] The medical patch according to any one of the above [1]-[5], wherein the polyfunctional monomer is one or a combination of two or more selected from the group consisting of ethylene glycol di(meth)acrylate, diethylene glycol di(meth)acrylate, triethylene glycol di(meth)acrylate, tetraethylene glycol di(meth)acrylate, polyethylene glycol (200) di(meth)acrylate, polyethylene glycol (400) di(meth)acrylate, dipropylene glycol di(meth)acrylate, tripropylene glycol di(meth)acrylate, polypropylene glycol (400) di(meth)acrylate, and 1,6-hexanediol di(meth)acrylate;

[7] The medical patch according to any one of the above [1]-[6], wherein the chain polymer portion comprises a hydroxy group-containing monomer;

[8] The medical patch according to the above [7], wherein the hydroxy group-containing monomer is one or a combination of two or more selected from the group consisting of 2-hydroxyethyl (meth)acrylate, 2-hydroxypropyl (meth)acrylate, and 4-hydroxybutyl (meth)acrylate;

[9] The medical patch according to the above [7] or [8], wherein the hydroxy value of the star-shaped acrylic block polymer is 5-50;

[10] The medical patch according to any one of the above [1]-[9], wherein the risperidone or a pharmaceutically acceptable salt thereof is risperidone free base;

[11] The medical patch according to any one of the above [1]-[10], wherein the carboxylic acid is one or a combination of two or more selected from carboxylic acids having 8 or more carbon atoms;

[12] The medical patch according to any one of the above [1]-[11], wherein the fatty acid ester is one or a combination of two or more selected from the group consisting of isopropyl myristate, diisopropyl adipate, myristyl myristate, octyldodecyl myristate, isopropyl palmitate, butyl stearate, hexyl laurate, decyl oleate, and diethyl sebacate;

[13] The medical patch according to any one of the above [1]-[12], wherein the content of the risperidone or a pharmaceutically acceptable salt thereof is 1-10% by mass, the content of the carboxylic acid is 1-10% by mass, the content of the fatty acid ester is 20-50% by mass, and the content of the adhesive is 40-70% by mass, in the adhesive composition;

[14] The medical patch according to any one of the above [1]-[13], which further comprises a surfactant in the adhesive composition;

[15] The medical patch according to the above [14], wherein the surfactant is one or a combination of two or more selected from the group consisting of polyoxyethylene sorbitan fatty acid esters, polyoxyethylene hydrogenated castor oils, polyoxyethylene alkyl ethers, polyethylene glycol fatty acid esters, and sorbitan fatty acid esters; and

[16] The medical patch according to the above [14] or [15], wherein the content of the surfactant in the adhesive composition is 1-10% by mass.

Also, other aspects of the present invention are as follows.

[17] The medical patch according to any one of the above [1]-[16], wherein the (meth)acrylic acid alkyl ester structural units having 7-17 carbon atoms account for 50-99.99% by mass of the whole structural units of the star-shaped acrylic block polymer;

[18] The medical patch according to any one of the above [1]-[17], wherein the polymerizable monomer further comprises one or a combination of two or more other polymerizable monomer(s);

[19] The medical patch according to any one of the above [1]-[18], wherein the (meth)acrylic acid alkyl ester having 7-17 carbon atoms is one or a combination of two selected from the group consisting of acrylic acid butyl ester and acrylic acid 2-ethylhexyl ester;

[20] The medical patch according to any one of the above [1]-[19], wherein the polyfunctional monomer is one or a combination of two selected from the group consisting of ethylene glycol diacrylate and tetraethylene glycol diacrylate;

[21] The medical patch according to any one of the above [1]-[20], wherein the carboxylic acid is one or a combination of two or more carboxylic acid(s) having 8 or more carbon atoms comprising caprylic acid;

[22] The medical patch according to any one of the above [1]-[21], wherein the fatty acid ester is one or a combination of two or more fatty acid ester(s) comprising isopropyl myristate; and

[23] The medical patch according to any one of the above [14]-[22], wherein the surfactant is one or a combination of two or more surfactant(s) comprising lauromacrogol.

Still other aspects of the present invention are as follows.

[24] The medical patch according to any one of the above [1]-[23], wherein the polymerizable monomer does not comprise a weakly basic monomer;

[25] The medical patch according to any one of the above [1]-[24], characterized in that the star-shaped acrylic block polymer in which at least three chain polymer portions radiate from a sulfur residue of a mercapto group situated at the center is produced by the steps comprising:

the first polymerization step in which the radical polymerization of the polymerizable monomers is carried out in the presence of a polyvalent mercaptan; and the second polymerization step in which the radical polymerization of an intermediate polymer obtained in said first polymerization step and the polymerizable monomers is carried out, wherein in the second reaction stage of the first polymerization step and the second polymerization step, the polymer solution obtained in the first polymerization step and the polymerizable monomers used in the second polymerization step are preliminarily collectively mixed, and the polymerization of the second reaction stage is carried out using the resulting mixed solution;

[26] The medical patch according to any one of the above [1]-[25] for use in the treatment of a psychiatric disorder (for example, schizophrenia, mania, and autism, in particular schizophrenia);

[27] A method for treating a psychiatric disorder (for example, schizophrenia, mania, and autism, in particular schizophrenia) comprising administering the medical patch according to any one of the above [1]-[25]; and

[28] A method for producing the medical patch according to any one of the above [1]-[25], characterized in that the method comprises the steps:

(a) producing a star-shaped acrylic block polymer by two steps of radical polymerization consisting of the first polymerization step and the second polymerization step using the same or different kind of polymerizable monomer in each elementary step of the radical polymerization steps in the presence of a polyvalent mercaptan, wherein in the second step of said two steps, a part of the polymer solution obtained in the first step and the polymerizable monomers used in the second step are polymerized, and then a monomer mixture comprising the remainder of the polymer solution obtained in the first step and the polymerizable monomers used in the second step is gradually added therein and mixed to be subjected to polymerization; and (b) mixing the star-shaped acrylic block polymer obtained in said (a) with risperidone or a pharmaceutically acceptable salt thereof, a carboxylic acid, and a fatty acid ester, and optionally other ingredient(s).

Still other aspects of the present invention are as follows.

2. Use of Star-Shaped Acrylic Block Polymer

[29] A star-shaped acrylic block polymer for use as an adhesive of a patch comprising an adhesive composition comprising risperidone or a pharmaceutically acceptable salt thereof, wherein the star-shaped acrylic block polymer has a star-shaped structure in which at least three chain polymer portions radiate from a sulfur residue of a mercapto group situated at the center, (meth)acrylic acid alkyl ester structural units having 7-17 carbon atoms account for 30-99.99% by mass of the whole structural units in said star-shaped acrylic block polymer, and at least one of said chain polymer portions has a structural unit having a copolymer structure of polymerizable monomers comprising a (meth)acrylic acid alkyl ester having 7-17 carbon atoms and a polyfunctional monomer;

[30] The star-shaped acrylic block polymer according to the above [29], wherein the adhesive composition comprises one or a combination of two or more ingredient(s) selected from carboxylic acids and fatty acid esters;

[31] The star-shaped acrylic block polymer according to the above [29] or [30], wherein the adhesive composition comprises a surfactant;

[32] The star-shaped acrylic block polymer according to the above [29] for use as an adhesive of the medical patch according to any one of the above [1]-[25];

[33] The star-shaped acrylic block polymer according to any one of the above [29]-[32] for improving the cohesive force or the thermostability of the adhesive composition;

[34] Use of a star-shaped acrylic block polymer in the manufacture of a patch comprising an adhesive composition comprising risperidone or a pharmaceutically acceptable salt thereof, wherein said star-shaped acrylic block polymer is a star-shaped acrylic block polymer having a star-shaped structure in which at least three chain polymer portions radiate from a sulfur residue of a mercapto group situated at the center, (meth)acrylic acid alkyl ester structural units having 7-17 carbon atoms account for 30-99.99% by mass of the whole structural units in said star-shaped acrylic block polymer, and at least one of said chain polymer portions has a structural unit having a copolymer structure of polymerizable monomers comprising a (meth)acrylic acid alkyl ester having 7-17 carbon atoms and a polyfunctional monomer;

[35] The use according to the above [34], wherein the adhesive composition comprises one or a combination of two or more ingredient(s) selected from carboxylic acids and fatty acid esters;

[36] The use according to the above [34] or [35], wherein the adhesive composition comprises a surfactant;

[37] The use according to the above [34], wherein the patch is the medical patch according to any one of the above [1]-[25];

[38] The use according to any one of the above [34]-[37], wherein the star-shaped acrylic block polymer improves the cohesive force or the thermostability of the adhesive composition;

[39] A method for improving the cohesive force or the thermostability of an adhesive composition of a patch comprising risperidone or a pharmaceutically acceptable salt thereof by using a star-shaped acrylic block polymer, wherein said star-shaped acrylic block polymer is a star-shaped acrylic block polymer having a star-shaped structure in which at least three chain polymer portions radiate from a sulfur residue of a mercapto group situated at the center, (meth)acrylic acid alkyl ester structural units having 7-17 carbon atoms account for 30-99.99% by mass of the whole structural units in said star-shaped acrylic block polymer, and at least one of said chain polymer portions has a structural unit having a copolymer structure of polymerizable monomers comprising a (meth)acrylic acid alkyl ester having 7-17 carbon atoms and a polyfunctional monomer;

[40] The method according to the above [39], wherein the adhesive composition comprises one or a combination of two or more ingredient(s) selected from carboxylic acids and fatty acid esters;

[41] The method according to the above [39] or [40], wherein the adhesive composition comprises a surfactant; and

[42] The method according to the above [39], wherein the patch is the medical patch according to any one of the above [1]-[25].

Effect of Invention

According to the present invention, a patch, which shows an excellent drug release from the formulation and excellent patch physical properties such as having a high cohesive force and causing no exudation of liquid components and no crystal precipitation of the drug etc. during long storage even if liquid components such as carboxylic acids and fatty acid esters are added thereto at a relatively large amount, and being able to be applied to a skin over a long period of time, can be provided by using a specific a star-shaped acrylic block polymer as an adhesive in a risperidone-containing patch.

Also, according to the risperidone-containing patch provided by the present invention, the drug can be absorbed into circulating blood via a skin in high efficiency, and side effects in gastrointestinal system due to oral administration and side effects which may be caused by the rapid increase in blood concentration can be avoided.

DESCRIPTION OF EMBODIMENTS

The medical patch of the present invention (also referred to as "risperidone-containing patch" in the present description) may be prepared by using a star-shaped acrylic block polymer as an adhesive, adding therein risperidone or a pharmaceutically acceptable salt thereof as an active ingredient, a carboxylic acid, and a fatty acid ester, and optionally other ingredient(s) to obtain an adhesive layer as a composition (i.e., adhesive composition), and laminating the adhesive layer on a backing.

Figure 1:
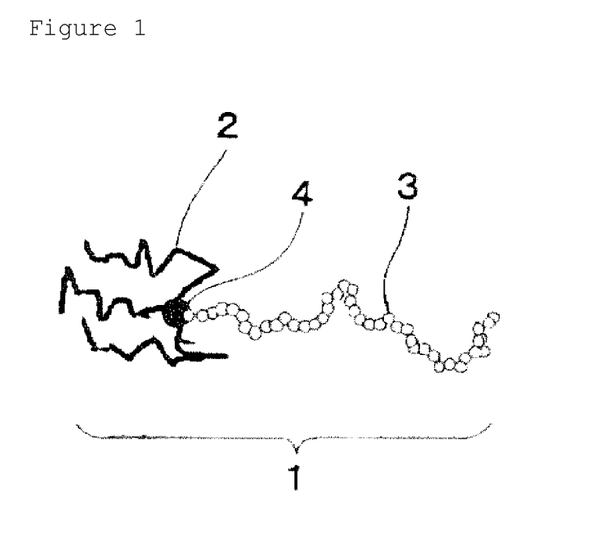
FIG. 1 shows an example of schematic diagram of a star-shaped acrylic block polymer of the present invention. The symbols in the figure means 1: a star-shaped structure, 2: chain polymer portions formed in the first polymerization step, 3: a chain polymer portion formed in the second polymerization step, and 4: a mercapto group.

The above star-shaped acrylic block polymer (also referred to as "star-shaped acrylic block copolymer") has a star-shaped structure in which at least three chain polymer portions radiate from a sulfur residue of a mercapto group situated at the center. Such star-shaped structure is also disclosed in documents (for example, JP 2842782 B2, JP 3385177 B2, JP 4603398 B2, JP 4744481 B2, and JP 4916200 B2). An example of schematic diagram of the star-shaped acrylic block polymer structure of the present invention is shown in FIG. 1. Also, (meth)acrylic acid alkyl ester structural units having 7-17 carbon atoms account for 30-99.99% by mass of the whole structural units in said star-shaped acrylic block polymer. The content of the (meth) acrylic acid alkyl ester structural units having 7-17 carbon atoms in the whole structural units of said star-shaped acrylic block polymer is preferably 50-99.99% by mass, 60-99.99% by mass, 35-97% by mass, more preferably 70-99.99% by mass, 40-95% by mass, still more preferably 50-85% by mass. When the content of the (meth)acrylic acid alkyl ester structural units having 7-17 carbon atoms in the whole structural units of said star-shaped acrylic block polymer is less than 50% by mass (typically less than 30% by mass), the polymer does not have a sufficient adhesive force. In the present description, "(meth)acrylic acid" means acrylic acid or methacrylic acid, and "structural unit(s)" in a polymer portion means unit(s) consisting of a structure derived from polymerizable monomers constituting the polymer. The sulfur residue of said mercapto group situated at the center means the backbone per se derived from a polyvalent mercaptan having said sulfur residue.

In the present description, for example, the expression of "X-Y % by mass" in a numerical range means "X % by mass or more to Y % by mass or less" unless otherwise specified.

Examples of the polymerizable monomer corresponding to the (meth)acrylic acid alkyl ester structural units having 7-17 carbon atoms (hereinafter also referred to as "(meth) acrylic acid alkyl ester monomer having 7-17 carbon atoms"), namely, (meth)acrylic acid alkyl ester having 7-17 carbon atoms include one or a combination of two or more selected from the group consisting of (meth)acrylic acid butyl ester, (meth)acrylic acid t-butyl ester, (meth)acrylic acid pentyl ester, (meth)acrylic acid hexyl ester, (meth) acrylic acid heptyl ester, (meth)acrylic acid octyl ester, (meth)acrylic acid isooctyl ester, (meth)acrylic acid nonyl ester, (meth)acrylic acid isononyl ester, (meth)acrylic acid decyl ester, (meth)acrylic acid undecyl ester, (meth)acrylic acid dodecyl ester, (meth)acrylic acid 2-ethylhexyl ester; and the like. Preferable examples of the (meth)acrylic acid alkyl ester monomer having 7-17 carbon atoms include (meth)acrylic acid butyl ester, (meth)acrylic acid t-butyl ester, (meth)acrylic acid 2-ethylhexyl ester, (meth)acrylic acid octyl ester, (meth)acrylic acid isooctyl ester, (meth) acrylic acid nonyl ester, and (meth)acrylic acid isononyl ester, more preferable examples thereof include a combination of (meth)acrylic acid butyl ester and (meth)acrylic acid 2-ethylhexyl ester, and still more preferable examples thereof include a combination of acrylic acid butyl ester and acrylic acid 2-ethylhexyl ester. When the (meth)acrylic acid alkyl ester monomer having 7-17 carbon atoms is used as a first polymerizable monomer and a second polymerizable monomer, they may be the same or different from each other.

In the present invention, a polyfunctional monomer is used in the production of the star-shaped acrylic block polymer. The polyfunctional monomer means a structural unit comprising a plurality of polymerizable partial structures such as a C=C bond. Examples of the polyfunctional monomer include one or a combination of two or more selected from the group consisting of bifunctional (meth) acrylates which are diester compounds of diols and (meth) acrylic acids such as alkylene glycol di(meth)acrylate, ethylene glycol di(meth)acrylate, diethylene glycol di(meth) acrylate, triethylene glycol di(meth)acrylate, tetraethylene glycol di(meth)acrylate, polyethylene glycol di(meth)acrylate (for example, polyethylene glycol (200) di(meth)acrylate, polyethylene glycol (400) di(meth)acrylate, and polyethylene glycol (600) di(meth)acrylate), propylene glycol di(meth)acrylate, dipropylene glycol di(meth)acrylate, tripropylene glycol di(meth)acrylate, polypropylene glycol di(meth)acrylate (for example, polypropylene glycol (400) di(meth)acrylate, polypropylene glycol (700) di(meth)acrylate, and polypropylene glycol (1000) di(meth)acrylate), 1,3-butylene glycol di(meth)acrylate, 1,4-butanediol di(meth)acrylate, 1,6-hexanediol di(meth)acrylate, neopentyl glycol di(meth)acrylate, 2-hydroxy-1,3-di(meth)acryloxypropane, 2,2-bis[4-(acryloxyethoxy)phenyl]propane, 2,2-bis[4-(methacryloxyethoxy)phenyl]propane, 2,2-bis[4-(acryloxy.polyethoxy)phenyl]propane, 2,2-bis[4-(methacryloxy.polyethoxy)phenyl]propane, and 2-hydroxy-1-acryloxy-3-methacryloxypropane; polyfunctional (meth) acrylates which are polyester compounds of compounds having 3 or more hydroxy groups per one molecule and (meth)acrylic acids such as trimethylolpropane tri(meth) acrylate, tetramethylolmethane tri(meth)acrylate, tetramethylolmethane tetra(meth)acrylate, pentaerythritol tetrakis (meth)acrylate, and dipentaerythritol hexakis(meth)acrylate; compounds having one or more allyl group(s) and one or more (meth)acryl group(s) per one molecule such as allyl (meth)acrylate; and compounds having two or more vinyl group(s) per one molecule such as divinylbenzene; and the like. Preferable examples of the polyfunctional monomer include bifunctional (meth)acrylates, and include one or a combination of two or more selected from the group consisting of ethylene glycol di(meth)acrylate, diethylene glycol di(meth)acrylate, triethylene glycol di(meth)acrylate, tetraethylene glycol di(meth)acrylate, polyethylene glycol (200) di(meth)acrylate, polyethylene glycol (400) di(meth) acrylate, dipropylene glycol di(meth)acrylate, tripropylene glycol di(meth)acrylate, polypropylene glycol (400) di(meth)acrylate, and 1,6-hexanediol di(meth)acrylate, more preferable examples thereof include one or a combination of two or more selected from the group consisting of ethylene glycol di(meth)acrylate and tetraethylene glycol di(meth) acrylate, further preferable examples thereof include ethylene glycol di(meth)acrylate, and particularly preferably examples thereof include ethylene glycol diacrylate. When the polyfunctional monomer is used as a first polymerizable monomer and a second polymerizable monomer, they may be the same or different from each other. A specific monomer (for example, 2-hydroxyethyl acrylate) may contain a certain amount of polyfunctional monomer(s) (for example, ethylene glycol diacrylate) as an impurity. In this regard, the polyfunctional monomer in the present invention may be added as a polyfunctional monomer per se, or may be a polyfunctional monomer contained as an impurity of another monomer.

The total content of the polyfunctional monomer in the whole structural units of the star-shaped acrylic block polymer is 0.001-1% by mass, preferably 0.002-0.5% by mass, more preferably 0.004-0.3% by mass, for example 0.01-1% by mass, 0.02-0.5% by mass, 0.04-0.3% by mass, or the like. Alternatively, the total content of the polyfunctional monomer in the whole structural units of the star-shaped acrylic block polymer is 0.001-1% by mass, preferably 0.002-0.5% by mass, more preferably 0.004-0.3% by mass, for example 0.01-1% by mass, 0.02-0.5% by mass, 0.04-0.3% by mass, or the like. When a specific monomer (for example, 2-hydroxyethyl acrylate) contains a certain amount of polyfunctional monomer(s) (for example, ethylene glycol diacrylate) as an impurity, the amount of the polyfunctional monomer to be introduced is adjusted in view of said amount contained as an impurity.

In one embodiment of the present invention, the polymerizable monomer does not comprise a weakly basic monomer. Such a weakly basic monomer means, for example, one or a combination of two or more selected from the group consisting of (meth)acrylates having a tertiary amine as a side chain, and amides. Examples of the weakly basic monomer include dialkylaminoalkyl (meth)acrylates such as dimethylaminoethyl (meth)acrylate and diethylaminoethyl (meth)acrylate; dialkylaminoalkyl (meth)acrylate quaternary ammonium salts such as dimethylaminoethyl (meth)acrylate quaternary ammonium salt: (meth)acrylamides such as dimethylaminopropyl acrylamide, diethylaminopropyl acrylamide, (meth)acrylamide, N-methyl (meth)acrylamide, and N-propyl (meth)acrylamide; and the like.

The chain polymer portion comprises a polymeric structure of radical polymerizable monomers, wherein the radical polymerizable monomers are, for example, (meth)acrylic acid alkyl ester monomers having 7-17 carbon atoms, polyfunctional monomers, and other polymerizable monomers.

The chain polymer portion of the star-shaped acrylic block polymer may comprise structural units derived from a polymerizable monomer other than the (meth)acrylic acid alkyl ester having 7-17 carbon atoms and the polyfunctional monomer (hereinafter referred to as "another polymerizable monomer (or other polymerizable monomers)") at the content of less than 70% by mass, preferably less than 50% by mass of the whole structural units.

Examples of the other polymerizable monomers include polymerizable monomers which are homopolymerizable or copolymerizable by radical polymerization, and include one or a combination of two or more selected from the group consisting of (meth)acrylic acid alkyl esters having 6 or less carbon atoms such as methyl (meth)acrylate and ethyl (meth)acrylate; hydroxy group-containing monomers such as 2-hydroxyethyl (meth)acrylate, 2-hydroxypropyl (meth)acrylate, and 4-hydroxybutyl (meth)acrylate; styrene monomers such as α-methylstyrene, vinyl toluene, and styrene; maleimide monomers such as phenylmaleimide and cyclohexylmaleimide; vinyl ether monomers such as methyl vinyl ether, ethyl vinyl ether, and isobutyl vinyl ether; fumaric acid monoalkyl esters and fumaric acid dialkyl esters; maleic acid monoalkyl esters and maleic acid dialkyl esters; itaconic acid monoalkyl esters and itaconic acid dialkyl esters; vinylpyrrolidones such as N-vinyl-2-pyrrolidone; (meth)acrylic acid alkoxy polyalkylene glycol esters such as methoxy triethylene glycol acrylate, methoxy polyethylene glycol methacrylate, ethoxy diethylene glycol acrylate, and methoxy polyethylene glycol acrylate; other vinyl compounds such as (meth)acrylonitrile, butadiene, isoprene, vinyl chloride, vinylidene chloride, vinyl acetate, vinyl ketone, vinyl pyridine, and vinyl carbazole; carboxyl group-containing monomers such as (meth)acrylic acid, fumaric acid, maleic acid, and itaconic acid; and the like. Preferable examples of the other polymerizable monomers include (meth)acrylic acid alkyl esters having 6 or less carbon atoms, hydroxy group-containing monomers, and vinyl compounds, more preferable examples thereof include methyl (meth)acrylate, ethyl (meth)acrylate, 2-hydroxyethyl (meth)acrylate, 2-hydroxypropyl (meth)acrylate, 4-hydroxybutyl (meth)acrylate, (meth)acrylonitrile, butadiene, isoprene, vinyl chloride, vinylidene chloride, vinyl acetate, vinyl ketone, vinyl pyridine, and vinyl carbazole, still more preferable examples thereof include methyl (meth)acrylate, 2-hydroxyethyl (meth)acrylate, or vinyl acetate, and particularly preferable examples thereof include methyl methacrylate, 2-hydroxyethyl acrylate, and vinyl acetate. When the other polymerizable monomers are used as a first polymerizable monomer and a second polymerizable monomer, they may be the same or different from each other.

In one typical embodiment of the star-shaped acrylic block polymer used in the patch of the present invention, the chain polymer portion comprises a hydroxy group-containing monomer, preferably comprises one or a combination of two or more selected from the group consisting of 2-hydroxyethyl (meth)acrylate, 2-hydroxypropyl (meth)acrylate, and 4-hydroxybutyl (meth)acrylate, more preferably comprises 2-hydroxyethyl (meth)acrylate, and particularly preferably comprises 2-hydroxyethyl acrylate.

In one typical embodiment of the star-shaped acrylic block polymer used in the patch of the present invention, the (meth)acrylic acid alkyl ester having 7-17 carbon atoms is one or a combination of two or more selected from the group consisting of (meth)acrylic acid butyl ester and (meth)acrylic acid 2-ethylhexyl ester, and a polyfunctional monomer which is one or a combination of two or more selected from the group consisting of ethylene glycol di(meth)acrylate and tetraethylene glycol di(meth)acrylate is contained in the star-shaped acrylic block polymer.

In the embodiment, the radical polymerizable monomer constituting a certain polymer portion in at least three or more chain polymer portions is one or a combination of two or more selected from the group consisting of (meth)acrylic acid alkyl esters having 6 or less carbon atoms, hydroxy group-containing monomers, and vinyl compounds.

In one typical embodiment of the star-shaped acrylic block polymer used in the patch of the present invention, the (meth)acrylic acid alkyl ester having 7-17 carbon atoms is a combination of acrylic acid butyl ester and acrylic acid 2-ethylhexyl ester, and a polyfunctional monomer which is one or a combination of two selected from the group consisting of ethylene glycol diacrylate and tetraethylene glycol diacrylate is contained in the star-shaped acrylic block polymer.

In the embodiment, the radical polymerizable monomer constituting a certain polymer portion in at least three or more chain polymer portions is one or a combination of two or more selected from the group consisting of methyl methacrylate, 2-hydroxyethyl acrylate, and vinyl acetate.

Due to the characteristic star-shaped acrylic block polymer structure, the star-shaped acrylic block polymer can achieve physical cross-linking caused by the microphase-separated structure, and achieve the balanced adhesive force and cohesive force without using a cross-linking agent.

Hereinafter, an especially appropriate method for producing the star-shaped acrylic block polymer is described.

Examples of the especially appropriate method for producing the star-shaped acrylic block polymer include a multistep radical polymerization method using a polyvalent mercaptan, wherein after the provision of all polymerizable monomers to a reaction system is completed, a polymerization initiator is subsequently added thereto. Such polymerization initiator subsequently added is referred to as "booster" in the present invention.

When the radical polymerization of the first polymerizable monomers (for example, any one of the (meth)acrylic acid alkyl ester monomers having 7-17 carbon atoms, the polyfunctional monomers, or the other polymerizable monomers, or a mixture thereof, preferably the other polymerizable monomers alone) is carried out in the presence of a polyvalent mercaptan, the first polymerizable monomers are radically polymerized from a sulfur residue of a mercapto group of a polyvalent mercaptan as an origin, and chain polymer portions radiate from the sulfur residue of the mercapto group (in other words, a polyvalent mercaptan having said sulfur residue) situated at the center to form a first star-shaped structure. In such case, a part of valence of the sulfur residue of the mercapto group of the polyvalent mercaptan is not used as an origin of the radical polymerization and remains unreacted. Subsequently, when the second polymerizable monomers (for example, any one of the (meth)acrylic acid alkyl ester monomers having 7-17 carbon atoms, the polyfunctional monomers, or the other polymerizable monomers, or a mixture thereof, preferably a mixture of the (meth)acrylic acid alkyl ester monomers having 7-17 carbon atoms, polyfunctional monomers, and the other polymerizable monomers) are added thereto to carry out the radical polymerization, the second polymerizable monomers are radically polymerized from the remaining sulfur residue of the mercapto group of the polyvalent mercaptan as an origin to form the second star-shaped structure different from the first star-shaped structure. As a result, the star-shaped acrylic block polymer of the present invention comprises at least three chain polymer portions.

In one typical embodiment of the method for producing the star-shaped acrylic block polymer of the present invention, in the first polymerization step, the polyvalent mercaptan is one or a combination of two or more selected from the group consisting of dipentaerythritol hexakisthioglycolate and dipentaerythritol hexakisthiopropionate (alias: dipentaerythritol-β-mercaptopropionate) (hereinafter abbreviated as DPMP), and the radical polymerizable monomer is another polymerizable monomer which is one or a combination of two or more selected from the group consisting of (meth)acrylic acid alkyl esters having 6 or less carbon atoms and vinyl compounds, and in the second polymerization step, the polymerizable monomer is a mixture of a (meth)acrylic acid alkyl ester having 7-17 carbon atoms which is one or a combination of two or more selected from the group consisting of (meth) acrylic acid butyl ester, (meth)acrylic acid t-butyl ester, and (meth)acrylic acid 2-ethylhexyl ester; another polymerizable monomer which is one or a combination of two or more selected from the group consisting of (meth)acrylic acid alkyl esters having 6 or less carbon atoms, hydroxy group-containing monomers, and vinyl compounds; and a polyfunctional monomer which is one or a combination of two or more selected from ethylene glycol di(meth)acrylate and tetraethylene glycol di(meth)acrylate.

In one typical embodiment of the method for producing the star-shaped acrylic block polymer of the present invention, in the first polymerization step, the polyvalent mercaptan is dipentaerythritol hexakisthiopropionate, and the radical polymerizable monomer is another polymerizable monomer which is one or a combination of two or more selected from the group consisting of methyl methacrylate and vinyl acetate, and in the second polymerization step, the polymerizable monomer is a mixture of (meth)acrylic acid alkyl ester having 7-17 carbon atoms which is one or a combination of two or more selected from the group consisting of acrylic acid butyl ester and acrylic acid 2-ethylhexyl ester; another polymerizable monomer which is one or a combination of two or more selected from the group consisting of methyl methacrylate, 2-hydroxyethyl acrylate, and vinyl acetate; and a polyfunctional monomer which is one or a combination of two or more selected from ethylene glycol di(meth) acrylate and tetraethylene glycol di(meth)acrylate.

In order to obtain the star-shaped acrylic block polymer, said multistep radical polymerization method especially preferably consists of two steps. Namely, said production method especially preferably comprises the first polymerization step in which the radical polymerization of the polymerizable monomers is carried out in the presence of the polyvalent mercaptan and the second polymerization step in which the radical polymerization of an intermediate polymer obtained in said first polymerization step and the polymerizable monomers is carried out, wherein (meth) acrylic acid alkyl ester having 7 or more carbon atoms accounts for 30-99.99% by mass of the total amount of all polymerizable monomers to be used, and a booster is added after the provision of all polymerizable monomers to a reaction system is completed.

In the second polymerization step, a polymer solution obtained in the first polymerization step is mixed with the polymerizable monomers used in the second polymerization step, and then polymerization is carried out.

In the second polymerization step, a polymer solution obtained in the first polymerization step and the polymerizable monomers used in the second polymerization step may be mixed at one time to be subjected to the polymerization, or the polymerizable monomers used in the second polymerization step may be gradually added to and mixed with a polymer solution obtained in the first polymerization step to be subjected to the polymerization.

In an especially preferable embodiment of the second polymerization step, to an initial preparation mixture (1) essentially comprising a part of (1a) a polymer solution obtained in the first polymerization step and (1b) the polymerizable monomers used in the second polymerization step is added a polymerization initiator to initiate the polymerization, and then a monomer mixture (2) essentially comprising the remainder of (2a) the polymer solution obtained in the first polymerization step and (2b) the polymerizable monomers used in the second polymerization step and a polymerization initiator are gradually added and mixed (preferably added dropwise and mixed) thereto, and after the addition and mixing are completed (namely, after the provision of all polymerizable monomers to the reaction system is completed), a booster is subsequently added thereto. Said method can sufficiently homogeneously mix the polymer solution obtained in the first polymerization step and the polymerizable monomers used in the second polymerization step.

When the polymerization initiator is added to the initial preparation mixture (1) to initiate the polymerization and then monomer mixture (2) and the polymerization initiator are gradually added and mixed thereto to initiate the polymerization, the addition and mixing are preferably carried out by dropwise, and the drop hour is preferably 20-300 minutes, more preferably 40-200 minutes, still more preferably 60-120 minutes. The temperature of the reaction system in the addition and mixing is preferably 30-200° C., more preferably 50-150° C.

The polymerization of the polymer solution (i.e., the above (1a) and (2a)) obtained in the first polymerization step is preferably stopped when the solution is used in the second polymerization step, and the total polymerization rate of the polymerizable monomers at that time is preferably 50-90%, more preferably 55-85%, still more preferably 60-80%. Examples of the method for stopping the polymerization include a method comprising adding a polymerization inhibitor to the polymer solution obtained in the first polymerization step, and a method comprising lowering the temperature of the polymer solution.

Examples of the polymerization inhibitor which may be used for stopping the polymerization include phenols such as hydroquinone, hydroquinone monomethyl ether, 2,5-bis (1,1,3,3-tetramethylbutyl)hydroquinone, 2,5-bis(1,1-dimethylbutyl)hydroquinone, methoxyphenol, 6-tert-butyl-2,4-xylenol, and 3,5-ditert-butylcatechol; N-nitroso phenylhydroxylamine aluminum salt; and phenothiazine, and any one of them may be used alone or in combination of two or more of them. Preferable examples of the polymerization inhibitor include phenols, and more preferable examples thereof include hydroquinone monomethyl ether. The total amount thereof to be used is preferably 1-10000 ppm, more preferably 10-1000 ppm, still more preferably 20-200 ppm relative to the polymerizable monomers used in the first polymerization step. When the total amount of the polymerization inhibitor to be used is less than 1 ppm, the polymerization may not be efficiently stopped. Meanwhile, when the total amount thereof to be used is more than 10000 ppm, the polymerization of the second polymerization step may not be initiated.

The polymerization of the first polymerization step can be substantially stopped by lowering the temperature of the polymer solution to 40° C. or less, because the degradation rate of the polymerization initiator depends on the temperature and thus a radical is hardly produced when the temperature of the polymer solution is 40° C. or less. In order to more certainly stop the polymerization, the temperature of the polymer solution may be lowered to 20° C. or less.

Hereinafter, raw materials used in a preferable method for producing the star-shaped acrylic block polymer are described in detail.

The (meth)acrylic acid alkyl ester having 7-17 carbon atoms accounts for 30-99.99% by mass (typically 50-99.99% by mass) in the total amount to be used of the polymerizable monomers which may be used in the present invention. The total content of the (meth)acrylic acid alkyl ester having 7-17 carbon atoms in all polymerizable monomers is preferably 60-99.99% by mass, 35-97.0% by mass, more preferably 70-99.99% by mass, 40-95.0% by mass, further preferably 80-99.99% by mass, 42-90.0% by mass, especially preferably 90-99.99% by mass, 50-86% by mass. When the total content of the (meth)acrylic acid alkyl ester having 7-17 carbon atoms in all polymerizable monomers is less than 50% by mass (typically less than 30% by mass), the obtained polymer does not have a sufficient adhesive force.

Preferable specific examples of the (meth)acrylic acid alkyl ester having 7-17 carbon atoms are as stated above, and any one of them may be used alone or in combination of two or more of them. The (meth)acrylic acid alkyl ester having 7-17 carbon atoms may be used in any step of the multistep radical polymerization steps, and preferably used in the second polymerization step (or the final polymerization step in case there are three or more polymerization steps).

The polymerizable monomer which may be used in the present invention may comprise a polymerizable monomer other than the (meth)acrylic acid alkyl ester having 7-17 carbon atoms (i.e., the polyfunctional monomers and the other polymerizable monomers) at the content of less than 70% by mass (typically less than 50% by mass) in the total amount to be used.

Preferable specific examples of the polyfunctional monomer are as stated above, and any one of them may be used alone or in combination of two or more of them. The polyfunctional monomer may be used in any step of the multistep radical polymerization steps, and preferably used in the second polymerization step (or the final polymerization step in case there are three or more polymerization steps).

The content of the polyfunctional monomer which may be used in the present invention in all polymerizable monomers is 0.001-1% by mass, preferably 0.002-0.5% by mass (typically 0.003-0.4% by mass), more preferably 0.004-0.3% by mass (typically 0.004-0.2% by mass), for example 0.01-1% by mass, 0.02-0.5% by mass (typically 0.03-0.4% by mass), 0.04-0.3% by mass (typically 0.04-0.2% by mass), or the like.

Also, the total content of the polyfunctional monomer is 0.001-1% by mass, preferably 0.002-0.5% by mass (typically 0.003-0.4% by mass), more preferably 0.004-0.3% by mass (typically 0.004-0.2% by mass), for example 0.01-1% by mass, 0.02-0.5% by mass (typically 0.03-0.4% by mass), 0.04-0.3% by mass (typically 0.04-0.2% by mass), or the like, relative to the whole structural units of said star-shaped acrylic block polymer.

Examples of the other polymerizable monomers include polymerizable monomers which are homopolymerizable or copolymerizable by radical polymerization, and preferable specific examples thereof are as stated above, and any one of them may be used alone or in combination of two or more of them. The other polymerizable monomers may be used in any step of the multistep radical polymerization steps, and preferably used in the first and the second polymerization steps (or all polymerization steps in case there are three or more polymerization steps).

When a hydroxy group-containing monomer is contained as another polymerizable monomer in the present invention, the hydroxy group-containing monomer is added so that the hydroxy value of the star-shaped acrylic block polymer will be 5-50, preferably 10-40, more preferably 15-35.

When a hydroxy group-containing monomer is contained as another polymerizable monomer in the present invention, the content thereof in all polymerizable monomers is 0.1-20% by mass, preferably 0.5-15% by mass, more preferably 1-10% by mass.

Also, the total content of the hydroxy group-containing monomer is 0.1-20% by mass, preferably 0.5-15% by mass, more preferably 1-10% by mass, relative to the whole structural units of said star-shaped acrylic block polymer.

In a preferable method for producing the star-shaped acrylic block polymer, the radical polymerization in the presence of a polyvalent mercaptan is carried out in multi-step comprising two or more steps, and different kinds of polymerizable monomers are preferably used in each elementary step. In this case, the "different kinds of polymerizable monomers" mean not only polymerizable monomers having different chemical structures, but also combinations of polymerizable monomers having the same chemical structure in different mixture ratio. Examples of using different kinds of polymerizable monomers in each elementary step include using a combination of polymerizable monomers consisting of methyl methacrylate (90 parts by mass) and butyl acrylate (10 parts by mass) in the first polymerization step, and a combination of polymerizable monomers consisting of methyl methacrylate (10 parts by mass) and butyl acrylate (90 parts by mass) in the second polymerization step. In this case, the obtained star-shaped acrylic block polymer has chain polymer portions having very different glass transition temperatures (Tg), and can sufficiently achieve the effects of the present invention, and has practically high performance.

Examples of the polyvalent mercaptan which may be used in the above method include diesters of diols such as ethylene glycol and 1,4-butanediol and carboxyl group-containing mercaptans such as ethylene glycol dithioglycolate, ethylene glycol dithiopropionate, 1,4-butanediol dithioglycolate, and 1,4-butanediol dithiopropionate; triesters of triols such as trimethylolpropane and carboxyl group-containing mercaptans such as trimethylolpropane trithioglycolate and trimethylolpropane trithiopropionate; polyesters of compounds having four hydroxy groups such as pentaerythritol and carboxyl group-containing mercaptans such as pentaerythritol tetrakisthioglycolate and pentaerythritol tetrakisthiopropionate; polyester compounds of compounds having six hydroxy groups such as dipentaerythritol and carboxyl group-containing mercaptans such as dipentaerythritol hexakisthioglycolate and dipentaerythritol hexakisthiopropionate (alias: dipentaerythritol-β-mercaptopropionate) (hereinafter abbreviated as DPMP); other polyester compounds of compounds having three or more hydroxy groups and carboxyl group-containing mercaptans; compounds having three or more mercapto groups such as trithioglycerin; triazine polyvalent thiols such as 2-di-n-butylamino-4,6-dimercapto-S-triazine and 2,4,6-trimercapto-S-triazine; compounds wherein hydrogen sulfide is added to two or more epoxy groups of polyvalent epoxy compounds to introduce two or more mercapto groups; ester compounds prepared by esterification of two or more carboxyl groups of polyvalent carboxylic acids and mercaptoethanol; and the like, and any one of them may be used alone or in combination of two or more of them. Preferable polyvalent mercaptan is a mercaptan having three or more valences, and preferable examples of the polyvalent mercaptan include polyester compounds of compounds having six hydroxy groups such as dipentaerythritol or compounds having four hydroxy groups such as pentaerythritol and carboxyl group-containing mercaptans, and more preferable examples thereof include dipentaerythritol hexakisthioglycolate, dipentaerythritol hexakisthiopropionate (alias: dipentaerythritol-β-mercaptopropionate) (hereinafter abbreviated as DPMP), pentaerythritol tetrakisthioglycolate, and pentaerythritol tetrakisthiopropionate, and more preferable examples thereof include dipentaerythritol hexakisthiopropionate. In said examples, "carboxyl group-containing mercaptans" mean compounds having one mercapto group and one carboxyl group such as thioglycolic acid, mercaptopropionic acid, and thiosalicylic acid.

In all polymerization steps, the temperature in carrying out the radical polymerization is preferably 30-200° C., more preferably 50-150° C.

A conventional polymerization initiator may be used in the radical polymerization. Examples of the polymerization initiator include azo initiators such as dimethyl-2,2'-azobis(2-methylpropionate) (abbreviated as V-601), 2,2'-azobisisobutyronitrile, 2,2'-azobis(2-methylbutyronitrile), 2,2'-azobis(2,4-dimethylvaleronitrile), and dimethyl 2,2'-azobisisobutyrate; peroxide polymerization initiators such as benzoyl peroxide; and the like, and any one of them may be used alone or in combination of two or more of them. Preferable examples of the polymerization initiator include dimethyl-2,2'-azobis(2-methylpropionate) (V-601). The total amount of the polymerization initiator to be used in the radical polymerization is preferably ⅓ or less, more preferably ⅕ or less of the amount of the polyvalent mercaptan by mass ratio. When the polymerization initiator is used at the amount more than the above ratio, many polymers are also produced from the polymerization initiator in addition to chain polymer portions produced from a sulfur residue of a mercapto group, and the production efficiency of the star-shaped acrylic block polymer easily decreases, and the physical properties of the obtained star-shaped acrylic block polymer are also easily impaired. The polymerization initiator may be added to the reaction system at one time or in several divided parts. In case of adding it in several divided parts, each part may be added at one time or added sequentially.

A conventional solvent may be used in the radical polymerization. Examples of the solvent include ester solvents such as ethyl acetate, propyl acetate, and butyl acetate; ketone solvents such as methyl ethyl ketone and cyclohexanone; aromatic solvents such as benzene and toluene; cellosolve solvents such as methyl cellosolve and ethyl cellosolve; and the like, and any one of them may be used alone or in combination of two or more of them.

In an especially preferable method for producing the star-shaped acrylic block polymer, a booster is preferably subsequently added after the provision of all polymerizable monomers used in the second polymerization step (or the final polymerization step in case there are three or more polymerization steps) to a reaction system is completed. Examples of the booster include the above polymerization initiators, and any one of them may be used alone or in combination of two or more of them. The total amount of the booster to be used is not especially limited, and preferably 0.1-5% by mass, more preferably 0.2-2% by mass, still more preferably 0.3-1% by mass relative to the total amount of the polymerizable monomers to be used. When the total amount of the booster to be used is less than 0.1% by mass, the booster cannot exert the effect. Meanwhile, using the total amount of more than 5% by mass of booster is uneconomical, because many substances having low molecular weight are produced, and the physical properties of the polymer are deteriorated. Examples of the method for adding the booster is not especially limited, and include the continuously dropping method in which the booster is continuously added dropwise, and the dividedly dropping method in which the booster is added at specific time interval. The temperature in adding the booster is not especially limited, and preferably 30-200° C., more preferably 50-150° C. The addition time of the booster is not especially limited, and preferably 1-10 hour(s), more preferably 2-8 hours.

After the addition of the booster is completed, the reaction system may be further maturated preferably at 30-200° C., more preferably at 50-150° C. Specifically, the maturation is preferably carried out under a reflux condition (i.e., within the above temperature range) of a solvent to be used. The maturation time is not especially limited, and preferably 1 hour or more, more preferably 2 hours or more, still more preferably 3 hours or more. The upper limit of the maturation time is not especially limited, and usually preferably within 20 hours.

In an especially preferable method for producing the star-shaped acrylic block polymer, the total time from the start of the polymerization to the completion of the above maturation in the second polymerization step is preferably 8-20 hours, more preferably 12-20 hours, still more preferably 15-20 hours. The total time of less than 8 hours from the start of the polymerization to the completion of the above maturation in the second polymerization step is not preferable, because the effects of the present invention cannot be sufficiently achieved in the obtained star-shaped acrylic block polymer, and especially, the remained amount of the (meth)acrylic acid alkyl ester having 7-17 carbon atoms increases. The total time of more than 20 hours from the start of the polymerization to the completion of the above maturation in the second polymerization step is also not preferable, because the productivity significantly decreases, the energy cost increases, and the performance of the obtained star-shaped acrylic block polymer may also decrease.

In addition to the above method, a general method used in a conventional method for producing a star-shaped acrylic block polymer may be appropriately used as a preferable method for producing the star-shaped acrylic block polymer.

The star-shaped acrylic block polymer is generally obtained as a polymer solution. When the star-shaped acrylic block polymer is obtained as a solution, the total non-volatile content in the solution is preferably 40-70% by mass, more preferably 45-65% by mass, still more preferably 45-60% by mass. When the total non-volatile content in the solution is less than 40% by mass, the viscosity of the solution decreases to cause the difficulty in coating the polymer, and such content is uneconomical because the amount of the solvent to be volatilized increases and much energy is required for drying. When the content thereof is more than 70% by mass, the viscosity of the solution significantly increases to cause the difficulty in handling.

In the present invention, any one of the above adhesives may be used alone or in a mixture or two or more of them. Among them, an acrylic polymer and a star-shaped acrylic block polymer are preferable, and the star-shaped acrylic block polymer is especially preferable because of the excellently balanced adhesive force and cohesive force. The adhesive is added to an adhesive composition in the total amount of 40-70% by mass, preferably 45-65% by mass, more preferably 50-60% by mass.

Risperidone which is contained in the adhesive composition of the patch of the present invention may be in the form of a free base, or in the form of a pharmaceutically acceptable salt. Examples of the pharmaceutically acceptable salt of risperidone include hydrochloride, sulfate, nitrate, phosphate, hydrobromide, acetate, propionate, citrate, lactate, oxalate, succinate, tartrate, malonate, fumarate, malate, benzoate, methanesulfonate, and saccharinate. Preferably, risperidone free base is added to the adhesive composition of the patch of the present invention. The risperidone or a pharmaceutically acceptable salt thereof is added to the adhesive composition at the amount of 1-10% by mass, preferably 2-8% by mass, more preferably 3-7% by mass.

The carboxylic acid to be added to the adhesive composition of the patch of the present invention functions as a solubilizer of risperidone and as a transdermal absorption enhancer. Examples of the carboxylic acid include aliphatic carboxylic acids having 1-7 carbon atoms (C1-C7) such as formic acid, acetic acid, propionic acid, butyric acid, levulinic acid, valeric acid, caproic acid, enanthic acid, lactic acid, maleic acid, fumaric acid, pyruvic acid, oxalic acid, malonic acid, succinic acid, glutaric acid, adipic acid, tartaric acid, sorbic acid, malic acid, and citric acid; aromatic carboxylic acids having 7 carbon atoms (C7) such as salicylic acid, benzoic acid, and gallic acid; aliphatic carboxylic acids having 8-18 carbon atoms (C8-C18) such as caprylic acid, pelargonic acid, capric acid, undecanoic acid, lauric acid, myristic acid, palmitic acid, margaric acid, stearic acid, isostearic acid, oleic acid, linoleic acid, and linolenic acid; aliphatic carboxylic acids having 20-22 carbon atoms (C20-C22) such as arachidonic acid, eicosapentaenoic acid, and docosahexaenoic acid; and aromatic carboxylic acids having 8-9 carbon atoms (C8-C9) such as phthalic acid, isophthalic acid, terephthalic acid, and cinnamic acid, and any one of them may be used alone or in combination of two or more of them. Preferable examples thereof include one or a combination of two or more selected from carboxylic acids having 8 or more carbon atoms, and more preferable examples thereof include one or a combination of two or more selected from C8-C18 aliphatic carboxylic acids. Still more preferable examples thereof include one or a combination of two or more carboxylic acid(s) selected from the group consisting of caprylic acid, pelargonic acid, capric acid, undecanoic acid, lauric acid, myristic acid, palmitic acid, stearic acid, isostearic acid, oleic acid, and linoleic acid, and particularly preferable examples thereof include caprylic acid. The total amount of the carboxylic acid to be added to the adhesive composition is 1-10% by mass, preferably 2-8% by mass, more preferably 3-7% by mass. The amount of the carboxylic acid to be added of less than 1% by mass is not preferable, because the sufficient drug solubility and the skin permeability of drug cannot be achieved. The amount of the carboxylic acid to be added of more than 10% by mass is also not preferable, because the cohesive force of the adhesive layer decreases, and a base material may remain on a skin.

The fatty acid ester to be added to the adhesive composition of the patch of the present invention as an essential ingredient functions as a transdermal absorption enhancer. Said fatty acid ester refers to a compound made from a fatty acid and a monovalent alcohol, namely a compound in which a fatty acid is fused to a monovalent alcohol, and does not include a compound which functions as a surfactant such as glycerin fatty acid esters as defined below. Examples of the fatty acid ester include isopropyl myristate, diisopropyl adipate, myristyl myristate, octyldodecyl myristate, isopropyl palmitate, butyl stearate, hexyl laurate, decyl oleate, and diethyl sebacate, and any one of them may be used alone or in combination of two or more of them. Preferable examples thereof include one or a combination of two or more selected from the group consisting of isopropyl myristate, diisopropyl adipate, and diethyl sebacate, and especially preferable examples thereof include isopropyl myristate. The total amount of said fatty acid ester to be added to the adhesive composition is 20-50% by mass, preferably 25-45% by mass, more preferably 30-40% by mass. The amount of said fatty acid ester to be added of less than 20% by mass is not preferable, because the sufficient skin permeability of drug cannot be achieved. The amount of said fatty acid ester to be added of more than 50% by mass is also not preferable, because the cohesive force of the adhesive layer decreases, and a base material may remain on a skin.

The surfactant which may be added to the adhesive composition of the patch of the present invention functions as a transdermal absorption enhancer. Said surfactant does not include the fatty acid ester as defined above. Examples of the surfactant include polyoxyethylene sorbitan fatty acid esters (for example, polyoxyethylene sorbitan monooleate), polyoxyethylene castor oils, polyoxyethylene hydrogenated castor oils, polyoxyethylene alkyl ethers (for example, lauromacrogol), polyoxyethylene alkylamine (for example, polyoxyethylene laurylamine), alkylalkanolamides (for example, lauric acid diethanolamide), alkyl ether carboxylates (for example, polyoxyethylene lauryl ether acetate), alkanesulfonates (for example, 1-hexanesulfonic acid sodium salt), fatty acid monoglyceride sulfates (for example, sodium lauroyl monoglyceride monosulfate), fatty acid amidoamine salts (for example, stearic acid diethylaminoethylamide), benzethonium chloride, sucrose fatty acid esters (for example, sucrose stearic acid ester), propylene glycol fatty acid esters (for example, propylene glycol monolaurate), polyethylene glycol fatty acid esters (for example, polyethylene glycol monolaurate), glycerin fatty acid esters (for example, glyceryl monostearate), polyglycerin fatty acid esters (for example, decaglycerin laurate), sorbitan fatty acid esters (for example, sorbitan monoleate), polyoxyethylene sorbitan fatty acid esters (for example, polyoxyethylene sorbitan monolaurate), and polyoxyethylene sorbitol fatty acid esters (for example, polyoxyethylene sorbitol tetraoleate), and any one of them may be used alone or in combination of two or more of them. Preferable examples thereof include one or a combination of two or more selected from the group consisting of polyoxyethylene sorbitan fatty acid esters (for example, polyoxyethylene sorbitan monoleate), polyoxyethylene hydrogenated castor oils, polyoxyethylene alkyl ethers (for example, lauromacrogol), polyethylene glycol fatty acid esters (for example, polyethylene glycol monolaurate), and sorbitan fatty acid esters (for example, sorbitan monoleate), and especially preferable examples thereof include lauromacrogol. The total amount of the surfactant to be added to the adhesive composition is 1-10% by mass, preferably 2-8% by mass, more preferably 2-7% by mass.

Another transdermal absorption enhancer may be further added to the adhesive composition of the patch of the present invention. Examples of the transdermal absorption enhancer include amines such as diisopropanolamine and triethanolamine; polyvalent alcohols such as glycols such as polyethylene glycol, propylene glycol, and butylene glycol; crotamiton; N-methylpyrrolidone; and the like, and any one of them may be used alone or in combination of two or more of them.

Further, an additive used in a conventional patch may be appropriately selected and used in the adhesive composition of the patch of the present invention if necessary in order to adjust the adhesive force and the stability of adhesive base. For example, water-soluble polymer(s) such as polyvinylpyrrolidone and polyvinyl alcohol; cellulose derivative(s) such as ethylcellulose, hydroxypropyl cellulose, and hydroxypropyl methylcellulose; silicon compound(s) such as anhydrous silicic acid and light anhydrous silicic acid; inorganic filler(s) such as zinc oxide, aluminum oxide, magnesium oxide, iron oxide, titanium dioxide, silica compounds, aluminum hydroxide, aluminum glycinate, dihydroxyaluminum aminoacetate, synthetic hydrotalcite, aluminometasilicate metal salt, and synthetic aluminum silicate; antioxidant(s) such as dibutylhydroxytoluene; and the like may be appropriately contained at an appropriate amount. Also, the adhesive composition of the patch of the present invention may comprise tackifier(s) such as polyterpene resins, petroleum resins, rosin resins, rosin ester resins, and oil-soluble phenol resins; softener(s) such as liquid paraffin, vaseline, polybutene, polyisobutylene, and polyisoprene; plasticizer(s) such as glycerol and sorbitol; and the like if necessary. Further, the adhesive composition of the patch of the present invention may comprise preservative(s) such as parahydroxybenzoic acid esters (for example, methyl parahydroxybenzoate); freshener(s) such as menthol; fungicide(s) such as ethanol and isopropyl alcohol; flavoring agent(s) such as mentha oil; coloring agent(s) such as yellow ferric oxide; and the like if necessary. These ingredients which may be used if necessary are not especially limited, and known ingredients may be appropriately used at an appropriate amount.

One typical embodiment of the patch of the present invention includes a medical patch comprising an adhesive composition consisting of
risperidone free base;
a carboxylic acid which is one or a combination of two or more selected from carboxylic acids having 8 or more carbon atoms;
a fatty acid ester which is one or a combination of two or more selected from the group consisting of isopropyl myristate, diisopropyl adipate, myristyl myristate, octyldodecyl myristate, isopropyl palmitate, butyl stearate, hexyl laurate, decyl oleate, and diethyl sebacate;
an adhesive;
optionally a surfactant which is one or a combination of two or more selected from the group consisting of polyoxyethylene sorbitan fatty acid esters, polyoxyethylene hydrogenated castor oils, polyoxyethylene alkyl ethers, polyethylene glycol fatty acid esters, and sorbitan fatty acid esters; and
optionally other ingredient(s)
wherein in the star-shaped acrylic block polymer used in said patch, the (meth)acrylic acid alkyl ester having 7-17 carbon atoms is one or a combination of two or more selected from the group consisting of (meth)acrylic acid butyl ester and (meth)acrylic acid 2-ethylhexyl ester, and a polyfunctional monomer which is one or a combination of two or more selected from the group consisting of ethylene glycol di(meth)acrylate and tetraethylene glycol di(meth)acrylate is contained therein.

In the embodiment, the radical polymerizable monomer constituting a certain polymer portion in at least three or more chain polymer portions is one or a combination of two or more selected from the group consisting of (meth)acrylic acid alkyl esters having 6 or less carbon atoms, hydroxy group-containing monomers, and vinyl compounds.

One typical embodiment of the patch of the present invention includes a medical patch comprising an adhesive composition consisting of
risperidone free base;
one or a combination of two or more carboxylic acid(s) having 8 or more carbon atoms comprising caprylic acid;
one or a combination of two or more fatty acid ester(s) comprising isopropyl myristate;
an adhesive;
optionally one or a combination of two or more surfactant(s) comprising lauromacrogol; and
optionally other ingredient(s)
wherein in the star-shaped acrylic block polymer used in said patch, the (meth)acrylic acid alkyl ester having 7-17 carbon atoms is a combination of acrylic acid butyl ester and acrylic acid 2-ethylhexyl ester, and a polyfunctional monomer which is one or a combination of two selected from the group consisting of ethylene glycol diacrylate and tetraethylene glycol diacrylate is contained therein.

In the embodiment, the radical polymerizable monomer constituting a certain polymer portion in at least three or more chain polymer portions is one or a combination of two or more selected from the group consisting of methyl methacrylate, 2-hydroxyethyl acrylate, and vinyl acetate.

The backing of the patch of the present invention is not especially limited, and an elastic or non-elastic backing usually used for a patch may be used. Specifically, a film or a sheet made from a synthetic resin such as polyethylene terephthalate, polyethylene, polypropylene, polybutadiene, ethylene vinyl acetate copolymer, polyvinyl chloride, polyester, nylon, and polyurethan, or a laminate thereof, a porous membrane, a foam, a woven fabric, a nonwoven fabric, a paper, or the like may be used.

In the patch of the present invention, the adhesive layer laminated on said backing is covered by a release liner, and the release liner is peeled off when the patch is used, and the surface of the adhesive layer is applied to a desired skin.

The release liner used in the patch of the present invention may be one usually used for a patch, and may be polyethylene terephthalate, polypropylene, a paper, or the like, and especially preferably polyethylene terephthalate. The release liner may be siliconized if necessary in order to optimize the peel force.

Also, the patch of the present invention may coexist with a deoxidant in order to enhance the stability of the drug during storage. Preferable examples of the deoxidant include a deoxidant made from iron and a deoxidant made from a non-ferrous metal. Examples of coexisting method of the deoxidant include a method wherein a deoxidant is directly included in a packaging container or a method wherein a deoxidizing film is laminated in a packaging container.

Examples of the method for producing the patch of the present invention include the following method. To a star-shaped acrylic block polymer are added risperidone or a pharmaceutically acceptable salt thereof and carboxylic acid(s), the resulting mixture is stirred and mixed until the risperidone or a pharmaceutically acceptable salt thereof is completely dissolved therein, then fatty acid ester(s) and optionally other ingredient(s) are added thereto, and the resulting mixture is homogeneously stirred and mixed to obtain an adhesive composition. The resulting adhesive composition is spread on a release liner or a backing to remove the solvent by drying and form an adhesive layer, and then the adhesive layer is covered by a backing or a release liner to obtain a patch of the present invention. The thickness of the adhesive layer is 100-300 μm, more preferably 150-250 μm. When the thickness is less than 100 μm, the drug-release is not sustained for a long period of time. When the thickness is more than 300 μm, the drug content in the adhesive layer increases, which would cause the increase in residual drug content and the increase in manufacturing cost.

Hereinafter, the present invention is described more in detail by way of Preparation Examples, Examples, and Test Examples, but the present invention is not limited to them. In the following Preparation Examples, Examples (Ex.), and Comparative Examples (Comp.), "part(s)" and "%" mean "part(s) by mass" and "% by mass" respectively, unless otherwise specified. Also, the number average molecular weight (Mn) and the weight average molecular weight (Mw) were calculated by gel permeation chromatography (GPC) in a polystyrene equivalent.

EXAMPLES

[Preparation of Acrylic Adhesive]

Preparation Example 1

1. Polymerization in the First Step: Synthesis of the Intermediate Polymer Solution To a four neck flask having a thermometer, a stirrer, an inert gas inlet tube, a reflux cooler, and a dropping funnel were added methyl methacrylate (24 parts), dipentaerythritol-β-mercaptopropionate (hereinafter abbreviated as DPMP) (1.2 parts), and ethyl acetate (24.82 parts) as a solvent. The resulting mixture was stirred under nitrogen stream and kept at 83±2° C., and to the mixture were added dimethyl-2,2'-azobis(2-methylpropionate) (trade name: V-601, manufactured by Wako Pure Chemical Industries, Ltd., hereinafter abbreviated as V-601) (0.048 part) as a polymerization initiator and ethyl acetate (0.432 part) as a solvent for dissolution to initiate the polymerization. After 30 minutes from the reaction initiation, to the mixture were added dropwise methyl methacrylate (56 parts) and ethyl acetate (15.25 parts) over 120 minutes, and added dropwise a V-601 solution (a mixture of V-601 (0.084 part), DPMP (2.8 parts), and ethyl acetate (2.8 parts)) over 90 minutes, and a reaction was carried out with controlling the internal temperature under reflux. After the addition of methyl methacrylate was completed, to the mixture was added ethyl acetate (2 parts), and the reaction was carried out for additional 130 minutes. Subsequently, to the mixture were added a polymerization inhibitor solution (a mixture consisting of hydroquinone monomethyl ether (0.04 part) and ethyl acetate (0.36 part)) and ethyl acetate (38.431 parts) for dilution, and the resulting mixture was cooled to obtain an intermediate polymer solution (A1) for an adhesive. The resulting intermediate polymer solution (A1) had a non-volatile content of 34.5%, and a viscosity of 90 mPa·s.

2. Reaction in the Second Step: Synthesis of Polymer for Adhesive

To a four neck flask having a thermometer, a stirrer, an inert gas inlet tube, a reflux cooler, and a dropping funnel were added the intermediate polymer solution (A1) (12.17 parts) obtained in the above reaction, butyl acrylate (15.53 parts), 2-ethylhexyl acrylate (5.48 parts), vinyl acetate (0.88 part), tetraethylene glycol diacrylate (0.03 part), and ethyl acetate (11.5 parts) as a solvent. The resulting mixture was stirred under nitrogen stream and kept at 83±2° C., and to the mixture was added a V-601 solution (a mixture of V-601 (0.01 part) and ethyl acetate (1 part)) as a polymerization initiator to initiate the polymerization. After 10 minutes from the reaction initiation, to the resulting mixture was added dropwise the intermediate polymer solution (A1) (18.26 parts), a monomer mixture consisting of butyl acrylate (23.3 parts), 2-ethylhexyl acrylate (8.22 parts), vinyl acetate (1.32 parts), tetraethylene glycol diacrylate (0.05 part), and ethyl acetate (10 parts) as a solvent, and a V-601 solution (a mixture of V-601 (0.02 part) and ethyl acetate (4 parts)) over 80 minutes, and a reaction was carried out with control under reflux. After completion of the addition, to the resulting mixture was added ethyl acetate (1 part), and the reaction was carried out for additional 3.5 hours. Subsequently, to the resulting mixture was added dropwise a V-601 solution (a mixture of V-601 (0.17 part) and ethyl acetate (12.3 parts)) as a booster over 1 hour, and the reaction was carried out under reflux for additional 10 hours. Subsequently, to the resulting mixture was added ethyl acetate (33 parts) as a dilution solvent, and the resulting mixture was cooled to obtain a polymer solution (B1) for an adhesive. The resulting polymer solution (B1) had a non-volatile content of 46.4%, and a viscosity of 4,360 mPa·s. The resulting polymer had a number average molecular weight (Mn) of 33,000, and a weight average molecular weight (Mw) of 428,000.

Preparation Example 2

Alternative Reaction in the Second Step: Synthesis of Polymer for Adhesive (Hydroxy Value=5.67)

To a four neck flask having a thermometer, a stirrer, an inert gas inlet tube, a reflux cooler, and a dropping funnel were added the intermediate polymer solution (A1) (12.17 parts) obtained in the above reaction, butyl acrylate (15.22 parts), 2-ethylhexyl acrylate (5.48 parts), vinyl acetate (0.88 part), 2-hydroxyethyl acrylate (0.33 part) (which comprises 0.19% by mass, i.e., 0.0006 part by mass of ethylene glycol diacrylate), tetraethylene glycol diacrylate (0.013 part), and ethyl acetate (11.5 parts) as a solvent. The resulting mixture was stirred under nitrogen stream and kept at 83±2° C., and to the mixture was added a V-601 solution (a mixture of V-601 (0.02 part) and ethyl acetate (1 part)) as a polymerization initiator to initiate the polymerization. After 10 minutes from the reaction initiation, to the resulting mixture was added dropwise the intermediate polymer solution (A1) (18.26 parts), a monomer mixture consisting of butyl acrylate (22.83 parts), 2-ethylhexyl acrylate (8.22 parts), vinyl acetate (1.32 parts), 2-hydroxyethyl acrylate (0.49 part) (which comprises 0.19% by mass, i.e., 0.0009 part by mass of ethylene glycol diacrylate), tetraethylene glycol diacrylate (0.020 part), and ethyl acetate (10 parts) as a solvent, and a V-601 solution (a mixture of V-601 (0.02 part) and ethyl acetate (4 parts)) over 80 minutes, and a reaction was carried out with control under reflux. After completion of the addition, to the resulting mixture was added ethyl acetate (1 part), and the reaction was carried out for additional 3.5 hours. Subsequently, to the resulting mixture was added dropwise a V-601 solution (a mixture of V-601 (0.17 part) and ethyl acetate (12.3 parts)) as a booster over 1 hour, and the reaction was carried out under reflux for additional 10 hours. Subsequently, to the resulting mixture was added ethyl acetate (23 parts) as a dilution solvent, and the resulting mixture was cooled to obtain a polymer solution (B2) for an adhesive. The resulting polymer solution (B2) had a non-volatile content of 49.5%, and a viscosity of 2,690 mPa·s. The resulting polymer had a number average molecular weight (Mn) of 32,000, and a weight average molecular weight (Mw) of 282,000.

Preparation Example 3

Alternative Reaction in the Second Step: Synthesis of Polymer for Adhesive

To a four neck flask having a thermometer, a stirrer, an inert gas inlet tube, a reflux cooler, and a dropping funnel were added the intermediate polymer solution (A1) (10.65 parts) obtained in the above reaction, butyl acrylate (13.61 parts), 2-ethylhexyl acrylate (4.79 parts), vinyl acetate (0.77 part), and ethyl acetate (15 parts) as a solvent. The resulting mixture was stirred under nitrogen stream and kept at 83±2° C., and to the mixture was added a V-601 solution (a mixture of V-601 (0.02 part) and ethyl acetate (1 part)) as a polymerization initiator to initiate the polymerization. After 10 minutes from the reaction initiation, to the resulting mixture was added dropwise the intermediate polymer solution (A1) (19.78 parts), a monomer mixture consisting of butyl acrylate (25.28 parts), 2-ethylhexyl acrylate (8.9 parts), vinyl acetate (1.42 parts), and ethyl acetate (16.6 parts) as a solvent, and a V-601 solution (a mixture of V-601 (0.02 part) and ethyl acetate (4 parts)) over 80 minutes, and a reaction was carried out with control under reflux. After completion of the addition, to the resulting mixture was added ethyl acetate (1 part), and the reaction was carried out for additional 3.5 hours. Subsequently, to the resulting mixture was added dropwise a V-601 solution (a mixture of V-601 (0.34 part) and ethyl acetate (4.3 parts)) as a booster over 1 hour, and the reaction was carried out under reflux for additional 10 hours. Subsequently, to the resulting mixture was added ethyl acetate (20 parts) as a dilution solvent, and the resulting mixture was cooled to obtain a polymer solution (B3) for an adhesive. The resulting polymer solution (B3) had a non-volatile content of 51.0%, and a viscosity of 2,010 mPa·s. The resulting polymer had a number average molecular weight (Mn) of 30,000, and a weight average molecular weight (Mw) of 163,000.

Preparation Example 4

Alternative Reaction in the Second Step: Synthesis of Polymer for Adhesive (Hydroxy Value=25.01)

To a four neck flask having a thermometer, a stirrer, an inert gas inlet tube, a reflux cooler, and a dropping funnel were added the intermediate polymer solution (A1) (12.17 parts) obtained in the above reaction, butyl acrylate (14.11 parts), 2-ethylhexyl acrylate (5.48 parts), vinyl acetate (0.88 part), 2-hydroxyethyl acrylate (1.45 parts) (which comprises 0.19% by mass, i.e., 0.0028 part by mass of ethylene glycol diacrylate), and ethyl acetate (11.5 parts) as a solvent. The resulting mixture was stirred under nitrogen stream and kept at 83±2° C., and to the mixture was added a V-601 solution (a mixture of V-601 (0.02 part) and ethyl acetate (1 part)) as a polymerization initiator to initiate the polymerization. After 10 minutes from the reaction initiation, to the resulting mixture was added dropwise the intermediate polymer solution (A1) (18.26 parts), a monomer mixture consisting of butyl acrylate (21.17 parts), 2-ethylhexyl acrylate (8.22 parts), vinyl acetate (1.32 parts), 2-hydroxyethyl acrylate (2.17 parts) (which comprises 0.19% by mass, i.e., 0.0041 part by mass of ethylene glycol diacrylate), and ethyl acetate (10 parts) as a solvent, and a V-601 solution (a mixture of V-601 (0.02 part) and ethyl acetate (4 parts)) over 80 minutes, and a reaction was carried out with control under reflux. After completion of the addition, to the resulting mixture was added ethyl acetate (1 part), and the reaction was carried out for additional 3.5 hours. Subsequently, to the resulting mixture was added dropwise a V-601 solution (a mixture of V-601 (0.08 part) and ethyl acetate (4.3 parts)) as a booster over 1 hour, and the reaction was carried out under reflux for additional 10 hours. Subsequently, to the resulting mixture was added ethyl acetate (31 parts) as a dilution solvent, and the resulting mixture was cooled to obtain a polymer solution (B4) for an adhesive. The resulting polymer solution (B4) had a non-volatile content of 48.3%, and a viscosity of 1,910 mPa·s. The resulting polymer had a number average molecular weight (Mn) of 37,000, and a weight average molecular weight (Mw) of 253,000.

Preparation Example 5

Alternative Reaction in the Second Step: Synthesis of Polymer for Adhesive (Hydroxy Value=16.67)

To a four neck flask having a thermometer, a stirrer, an inert gas inlet tube, a reflux cooler, and a dropping funnel were added the intermediate polymer solution (A1) (12.17 parts) obtained in the above reaction, butyl acrylate (14.59 parts), 2-ethylhexyl acrylate (5.48 parts), vinyl acetate (0.88 part), 2-hydroxyethyl acrylate (0.97 part) (which comprises 0.19% by mass, i.e., 0.0018 part by mass of ethylene glycol diacrylate), and ethyl acetate (11.5 parts) as a solvent. The resulting mixture was stirred under nitrogen stream and kept at 83±2° C., and to the mixture was added a V-601 solution (a mixture of V-601 (0.02 part) and ethyl acetate (1 part)) as a polymerization initiator to initiate the polymerization. After 10 minutes from the reaction initiation, to the resulting mixture was added dropwise the intermediate polymer solution (A1) (18.26 parts), a monomer mixture consisting of butyl acrylate (21.89 parts), 2-ethylhexyl acrylate (8.22 parts), vinyl acetate (1.32 parts), 2-hydroxyethyl acrylate (1.45 parts) (which comprises 0.19% by mass, i.e., 0.0028 part by mass of ethylene glycol diacrylate), and ethyl acetate (10 parts) as a solvent, and a V-601 solution (a mixture of V-601 (0.02 part) and ethyl acetate (4 parts)) over 80 minutes, and a reaction was carried out with control under reflux. After completion of the addition, to the resulting mixture was added ethyl acetate (1 part), and the reaction was carried out for additional 3.5 hours. Subsequently, to the resulting mixture was added dropwise a V-601 solution (a mixture of V-601 (0.08 part) and ethyl acetate (4.3 parts)) as a booster over 1 hour, and the reaction was carried out under reflux for additional 10 hours. Subsequently, to the resulting mixture was added ethyl acetate (31 parts) as a dilution solvent, and the resulting mixture was cooled to obtain a polymer solution (B5) for an adhesive. The resulting polymer solution (B5) had a non-volatile content of 48.6%, and a viscosity of 2,250 mPa·s. The resulting polymer had a number average molecular weight (Mn) of 39,000, and a weight average molecular weight (Mw) of 278,000.

Preparation Example 6

Alternative Reaction in the Second Step: Synthesis of Polymer for Adhesive (Hydroxy Value=33.35)

To a four neck flask having a thermometer, a stirrer, an inert gas inlet tube, a reflux cooler, and a dropping funnel were added the intermediate polymer solution (A1) (12.17 parts) obtained in the above reaction, butyl acrylate (13.63 parts), 2-ethylhexyl acrylate (5.48 parts), vinyl acetate (0.88 part), 2-hydroxyethyl acrylate (1.93 parts) (which comprises 0.19% by mass, i.e., 0.0037 part by mass of ethylene glycol diacrylate), and ethyl acetate (11.5 parts) as a solvent. The resulting mixture was stirred under nitrogen stream and kept at 83±2° C., and to the mixture was added a V-601 solution (a mixture of V-601 (0.02 part) and ethyl acetate (1 part)) as a polymerization initiator to initiate the polymerization. After 10 minutes from the reaction initiation, to the resulting mixture was added dropwise the intermediate polymer solution (A1) (18.26 parts), a monomer mixture consisting of butyl acrylate (20.44 parts), 2-ethylhexyl acrylate (8.22 parts), vinyl acetate (1.32 parts), 2-hydroxyethyl acrylate (2.90 parts) (which comprises 0.19% by mass, i.e., 0.0055 part by mass of ethylene glycol diacrylate), and ethyl acetate (10 parts) as a solvent, and a V-601 solution (a mixture of V-601 (0.02 part) and ethyl acetate (4 parts)) over 80 minutes, and a reaction was carried out with control under reflux. After completion of the addition, to the resulting mixture was added ethyl acetate (1 part), and the reaction was carried out for additional 3.5 hours. Subsequently, to the resulting mixture was added dropwise a V-601 solution (a mixture of V-601 (0.08 part) and ethyl acetate (4.3 parts)) as a booster over 1 hour, and the reaction was carried out under reflux for additional 10 hours. Subsequently, to the resulting mixture was added ethyl acetate (31 parts) as a dilution solvent, and the resulting mixture was cooled to obtain a polymer solution (B6) for an adhesive. The resulting polymer solution (B6) had a non-volatile content of 48.8%, and a viscosity of 1,790 mPa·s. The resulting polymer had a number average molecular weight (Mn) of 40,000, and a weight average molecular weight (Mw) of 295,000.

Preparation Example 7

Alternative Reaction in the Second Step: Synthesis of Polymer for Adhesive (Hydroxy Value=16.67)

To a four neck flask having a thermometer, a stirrer, an inert gas inlet tube, a reflux cooler, and a dropping funnel are added the intermediate polymer solution (A1) (12.17 parts) obtained in the above reaction, butyl acrylate (14.59 parts), 2-ethylhexyl acrylate (5.48 parts), vinyl acetate (0.88 part), 2-hydroxyethyl acrylate (0.97 part) (which comprises 0.19% by mass, i.e., 0.0018 part by mass of ethylene glycol diacrylate), ethylene glycol diacrylate (0.0019 part), and ethyl acetate (11.5 parts) as a solvent. The resulting mixture is stirred under nitrogen stream and kept at 83±2° C., and to the mixture is added a V-601 solution (a mixture of V-601 (0.02 part) and ethyl acetate (1 part)) as a polymerization initiator to initiate the polymerization. After 10 minutes from the reaction initiation, to the resulting mixture is added dropwise the intermediate polymer solution (A1) (18.26 parts), a monomer mixture consisting of butyl acrylate (21.89 parts), 2-ethylhexyl acrylate (8.22 parts), vinyl acetate (1.32 parts), 2-hydroxyethyl acrylate (1.45 parts) (which comprises 0.19% by mass, i.e., 0.0028 part by mass of ethylene glycol diacrylate), ethylene glycol diacrylate (0.0027 part), and ethyl acetate (10 parts) as a solvent, and a V-601 solution (a mixture of V-601 (0.02 part) and ethyl acetate (4 parts)) over 80 minutes, and a reaction is carried out with control under reflux. After completion of the addition, to the resulting mixture is added ethyl acetate (1 part), and the reaction is carried out for additional 3.5 hours. Subsequently, to the resulting mixture is added dropwise a V-601 solution (a mixture of V-601 (0.08 part) and ethyl acetate (4.3 parts)) as a booster over 1 hour, and the reaction is carried out under reflux for additional 10 hours. Subsequently, to the resulting mixture is added ethyl acetate (31 parts) as a dilution solvent, and the resulting mixture is cooled to obtain a polymer solution (B7) for an adhesive.

Also, the properties used in the above Preparation Examples were measured and evaluated by the following methods.

[Measurement Methods of Specs of Adhesives]

(1) Viscosity

Viscosity was measured by a type B viscometer at 25° C. The number of revolutions was 12 revolutions per minute.

(2) Non-Volatile Content

A mixture was dried at 150° C. for 15 minutes in a circulating hot air dryer, and a non-volatile content was calculated by mass change.

[Hydroxy Value of Polymer]

A hydroxy value of polymer means the amount of potassium hydroxide (mg) corresponding to the hydroxy groups contained in 1 g of said polymer, namely the amount of potassium hydroxide (KOH) (mg) required for neutralizing acetic acid which is bound to the hydroxy groups when the hydroxy groups contained in 1 g of said polymer are acetylated. For example, regarding a polymer prepared by polymerizing monomer ingredients comprising 1% by mass of 2-hydroxyethyl acrylate as a hydroxy group-containing monomer, the hydroxy value of said polymer can be calculated on the basis of the following equation.

[Hydroxy value of polymer]=[0.01 (content of 2-hydroxyethyl acrylate in monomer ingredients used as a raw material of polymer)/116 (molecular weight of 2-hydroxyethyl acrylate)]× 56100=4.8 mg KOH/g    Equation:

The hydroxy value of polymer can be easily adjusted by adjusting the amount of the hydroxy group-containing monomer contained in the monomer ingredients used as a raw material of said polymer.

[Preparation of Patch]

Examples 1-3

To the acrylic adhesive of the Preparation Example 1 were added risperidone free base and caprylic acid, the resulting mixture was stirred and mixed until risperidone was completely dissolved therein, then lauromacrogol and isopropyl myristate were added thereto, the resulting mixture was homogeneously stirred and mixed to obtain an adhesive composition, the resulting adhesive composition was spread on a release liner to remove the solvent by drying and form an adhesive layer having a thickness of 200 μm, and then the adhesive layer was covered by a backing to obtain a patch. The mixing ratio (%) of each ingredient is shown in Table 1-1.

Examples 4-5

Each patch of Examples 4 and 5 was obtained according to the same preparation method as Example 1 using the acrylic adhesive of the Preparation Example 2. The mixing ratio (%) of each ingredient is shown in Table 1-1.

Comparative Examples 1-2

Each patch of Comparative Examples 1 and 2 was obtained according to the same preparation method as Example 1 using DURO-TAK 87-4098 (manufacture by Henkel AG & Co. KGaA) or MAS-811 (manufactured by CosMED Pharmaceutical Co. Ltd.), each of which is an acrylic adhesive containing no functional group. The mixing ratio (%) of each ingredient is shown in Table 1-2.

Comparative Example 3

The patch of Comparative Example 3 was obtained according to the same preparation method as Example 1 using the acrylic adhesive of the Preparation Example 3. The mixing ratio (%) of each ingredient is shown in Table 1-2.

TABLE 1-1

| Ingredient | Ex. 1 | Ex. 2 | Ex. 3 | Ex. 4 | Ex. 5 |
|---|---|---|---|---|---|
| Acrylic adhesive of Preparation Example 1 | 50.6 | 53.1 | 55.6 | — | — |
| Acrylic adhesive of Preparation Example 2 | — | — | — | 50.6 | 51.8 |
| Lauromacrogol | 5.0 | 2.5 | — | 5.0 | 5.0 |
| Isopropyl myristate | 35.0 | 35.0 | 35.0 | 35.0 | 35.0 |
| Caprylic acid | 5.4 | 5.4 | 5.4 | 5.4 | 4.7 |
| Risperidone free base | 4.0 | 4.0 | 4.0 | 4.0 | 3.5 |
| Total | 100 | 100 | 100 | 100 | 100 |

TABLE 1-2

| Ingredient | Comp. 1 | Comp. 2 | Comp. 3 |
|---|---|---|---|
| DURO-TAK 87-4098 | 50.6 | — | — |
| MAS-811 | — | 50.6 | — |
| Acrylic adhesive of Preparation Example 3 | — | — | 50.6 |
| Lauromacrogol | 5.0 | 5.0 | 5.0 |
| Isopropyl myristate | 35.0 | 35.0 | 35.0 |
| Caprylic acid | 5.4 | 5.4 | 5.4 |
| Risperidone free base | 4.0 | 4.0 | 4.0 |
| Total | 100 | 100 | 100 |

Examples 6-7

To the acrylic adhesive of the Preparation Example 4 were added risperidone free base and caprylic acid, the resulting mixture was stirred and mixed until risperidone was completely dissolved therein, then lauromacrogol and isopropyl myristate were added thereto, the resulting mixture was homogeneously stirred and mixed to obtain an adhesive composition, the resulting adhesive composition was spread on a release liner to remove the solvent by drying and form an adhesive layer having a thickness of 175 μm, then the resulting adhesive layer was covered by a backing to obtain a patch. The mixing ratio (%) of each ingredient is shown in Table 2-1.

Example 8

A patch of Example 8 was obtained according to the same preparation method as Example 6 using the acrylic adhesive of the Preparation Example 5. The mixing ratio (%) of each ingredient is shown in Table 2-1.

Examples 9-10

Each patch of Examples 9 and 10 was obtained according to the same preparation method as Example 6 using the acrylic adhesive of the Preparation Example 6. The mixing ratio (%) of each ingredient is shown in Table 2-1.

Comparative Examples 4-5

Each patch of Comparative Examples 4 and 5 was obtained according to the same preparation method as Example 6 using an acrylic adhesive DURO-TAK 87-4098 (manufacture by Henkel AG & Co. KGaA) or MAS-811 (manufactured by CosMED Pharmaceutical Co. Ltd.). The mixing ratio (%) of each ingredient is shown in Table 2-2.

TABLE 2-1

| Ingredient | Ex. 6 | Ex. 7 | Ex. 8 | Ex. 9 | Ex. 10 |
|---|---|---|---|---|---|
| Acrylic adhesive of Preparation Example 4 | 50.6 | 58.0 | — | — | — |
| Acrylic adhesive of Preparation Example 5 | — | — | 58.0 | — | — |
| Acrylic adhesive of Preparation Example 6 | — | — | — | 58.0 | 48.9 |
| Lauromacrogol | 5.0 | 5.0 | 5.0 | 5.0 | 5.0 |
| Isopropyl myristate | 35.0 | 25.0 | 25.0 | 25.0 | 35.0 |
| Caprylic acid | 5.4 | 7.0 | 7.0 | 7.0 | 5.7 |
| Risperidone free base | 4.0 | 5.0 | 5.0 | 5.0 | 5.4 |
| Total | 100 | 100 | 100 | 100 | 100 |

TABLE 2-2

| Ingredient | Comp. 4 | Comp. 5 |
|---|---|---|
| DURO-TAK 87-4098 | 50.6 | — |
| MAS-811 | — | 50.6 |
| Lauromacrogol | 5.0 | 5.0 |
| Isopropyl myristate | 35.0 | 35.0 |
| Caprylic acid | 5.4 | 5.4 |
| Risperidone free base | 4.0 | 4.0 |
| Total | 100 | 100 |

Example 11

A patch of Example 11 is obtained according to the same preparation method as Example 8 using the acrylic adhesive of the Preparation Example 7. The mixing ratio (%) of each ingredient is shown in Table 3.

TABLE 3

| Ingredient | Ex. 11 |
|---|---|
| Acrylic adhesive of Preparation Example 7 | 58.0 |
| Lauromacrogol | 5.0 |
| Isopropyl myristate | 25.0 |
| Caprylic acid | 7.0 |
| Risperidone free base | 5.0 |
| Total | 100 |

[Test Example 1]: Cohesive Force Test

In order to evaluate the adhesive property of the patch of the present invention, each patch of Examples 1-10 and Comparative Examples 1-5 was subjected to a cohesive force test. After 24 hours from the preparation of each formulation, the adhesive layer surface of the formulation was pressed by a finger, the finger was took off from the surface, then the condition (smooth or undulating) of the adhesive layer of the formulation surface or an adhesive layer residue on the skin was visually observed. A test formulation in which the condition of the adhesive layer was smooth and there was no adhesive layer residue on the skin after the test was evaluated as a formulation having a good cohesive force (•), a test formulation in which the condition of the adhesive layer was undulating or uneven and there was slight amount of adhesive layer residue on the skin after the test was evaluated as a formulation having a slightly poor cohesive force (▲), and a test formulation in which the condition of the adhesive layer was undulating or clearly uneven and there was an adhesive layer residue on the skin after the test was evaluated as a formulation having a poor cohesive force (x). These results are shown in Tables 4-1 and 4-2.

TABLE 4-1

| Test formulation | Evaluation results of cohesive force |
|---|---|
| Example 1 | • |
| Example 2 | • |
| Example 3 | • |
| Example 4 | • |
| Example 5 | • |
| Comparative Example 1 | x |
| Comparative Example 2 | x |
| Comparative Example 3 | ▲ |

TABLE 4-2

| Test formulation | Evaluation results of cohesive force |
|---|---|
| Example 6 | • |
| Example 7 | • |
| Example 8 | • |
| Example 9 | • |
| Example 10 | • |
| Comparative Example 4 | x |
| Comparative Example 5 | x |

As shown in the test results in Table 4-1 and 4-2, each patch of the present invention showed a higher cohesive force as compared to each patch of Comparative Examples. Also, the patch of Example 11 can be subject to the same test to confirm its high cohesive force. Namely, each patch of the present invention can maintain a good cohesive force and shows an excellent adhesive property, in spite of comprising a large amount of liquid additive(s).

[Test Example 2]: Thermostability Test

In order to evaluate the thermostability of the adhesive layer of the patch of the present invention, each patch of Example 1 and Comparative Example 3 was subjected to a thermostability test. Each one test formulation cut into a square shape having a size of 23 mm×23 mm was packed per a pouch and stored at 60° C. for 1 week, then fluidity (cold flow) of the adhesive layer and the adhesion of the adhesive layer to the inside of the packing pouch were visually observed. After the storage at 60° C. for 1 week, a test formulation in which there was almost no fluidity of the adhesive layer and no adhesion of the adhesive layer to the packing pouch was evaluated as a formulation having good thermostability (•), a test formulation in which the adhesive layer is slightly spread out of the edge of the formulation and slightly adhered to the packing pouch was evaluated as a formulation having slightly poor thermostability (▲), and a test formulation in which the adhesive layer is clearly spread out of the edge of the formulation and adhered to the packing pouch, and which cannot be take out from the pouch was evaluated as a formulation having poor thermostability (x). These results are shown in Table 5.

TABLE 5

| Test formulation | Evaluation results of thermostability |
|---|---|
| Example 1 | • |
| Comparative Example 3 | x |

As shown in the test results in Table 5, the patch of the present invention showed higher thermostability as compared to the patch of Comparative Example 3. Also, each patch of other Examples can be subjected to the same test to confirm their high thermostability. Namely, each patch of the present invention maintains the excellent effects of the present invention even at an extreme storage condition of a high temperature storage condition, in spite of comprising a large amount of liquid additive(s).

[Test Example 3]: Evaluation of Crystal Precipitation of Drug

In order to evaluate the crystal precipitation in the patch of the present invention with lapse of time, each patch of Examples 6-10 and Comparative Examples 3-5 was stored at 20° C. for 1 month, and then the adhesive layer surface was visually and microscopically observed. A formulation in which there was no crystal precipitation of risperidone after the storage at 20° C. for 1 month was evaluated as a formulation having good solubility (•), and a formulation in which the crystal precipitation of risperidone was observed was evaluated as a formulation having poor solubility (x). These results are shown in Table 6.

TABLE 6

| Test formulation | Evaluation results of crystal precipitation |
|---|---|
| Example 6 | • |
| Example 7 | • |

TABLE 6-continued

| Test formulation | Evaluation results of crystal precipitation |
|---|---|
| Example 8 | ● |
| Example 9 | ● |
| Example 10 | ● |
| Comparative Example 3 | x |
| Comparative Example 4 | x |
| Comparative Example 5 | x |

As shown in the results in Table 6, crystal(s) of risperidone precipitated in each patch of Comparative Examples 3-5 after the storage at 20° C. for 1 month, while no crystal was observed in each patch of Examples 6-10 after the storage at 20° C. for 1 month. Also, the patch of Example 11 can also be subjected to the same test to confirm that said patch can suppress the crystal precipitation. Each patch of the present invention has more excellent drug solubility to suppress the crystal precipitation with lapse of time as compared to each patch of Comparative Examples.

[Test Example 4]: In Vitro Hairless Rat Skin Permeability Test

Figure 2:
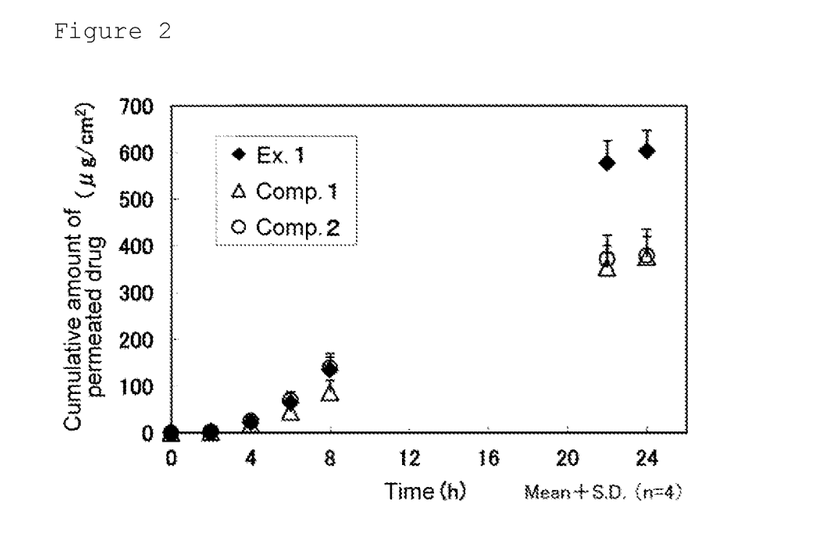
FIG. 2 shows the cumulative amount of permeated drug in the skin permeability test of Test Example 4.
Figure 3:
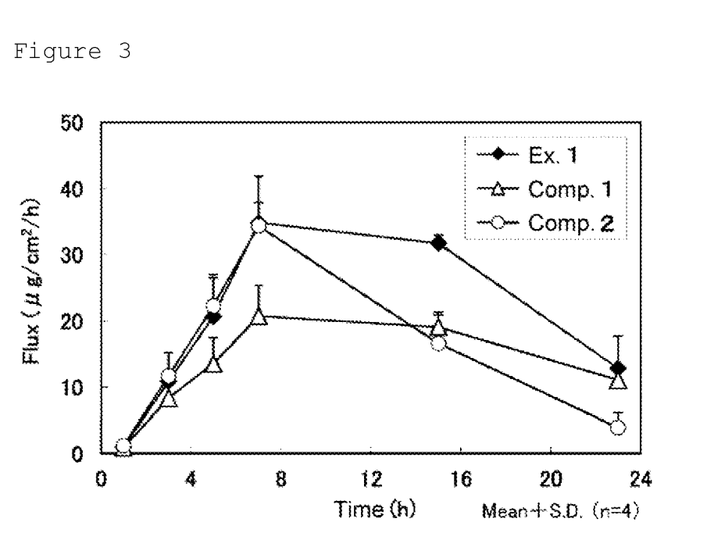
FIG. 3 shows the transdermal absorption rate of drug (Flux) in the skin permeability test of Test Example 4.

In order to evaluate the transdermal absorbability of risperidone for the patch of the present invention, each patch of Examples 1-10, and Comparative Examples 1, 2, 4, and 5 was subjected to an in vitro skin permeability test using a hairless rat skin. An excised abdominal skin of a hairless rat (HWY series, 7 weeks old) was put in a Franz diffusion cell, and each test formulation cut into a round shape ($\varphi$ 14 mm) was applied thereto. The receptor side was filled with phosphate buffered saline, and hot water of 37° C. was circulated in the water jacket. The receptor solution was sampled with lapse of time after the test start until 24 hours, the amount of risperidone permeated the skin was measured by liquid chromatography, and the measurement result was used to calculate the cumulative amount of permeated drug ($\mu g/cm^2$) and transdermal absorption rate of drug (Flux: $\mu g/cm^2/h$). These results are shown in Tables 7-1 and 7-2. Also, regarding each patch of Example 1, and Comparative Examples 1 and 2, the cumulative amount of permeated drug with lapse of time is shown in FIG. 2, and Flux with lapse of time is shown in FIG. 3.

TABLE 7-1

| Test formulation | Cumulative amount of permeated drug after 24 hours ($\mu g/cm^2$) | Maximum transdermal absorption rate of drug ($\mu g/cm^2/h$) |
|---|---|---|
| Example 1 | 603.9 | 34.82 |
| Example 2 | 584.1 | 32.36 |
| Example 3 | 492.9 | 26.52 |
| Example 4 | 603.0 | 34.00 |
| Example 5 | 492.9 | 27.57 |
| Comparative Example 1 | 375.7 | 20.71 |
| Comparative Example 2 | 379.2 | 34.35 |

TABLE 7-2

| Test formulation | Cumulative amount of permeated drug after 24 hours ($\mu g/cm^2$) | Maximum transdermal absorption rate of drug ($\mu g/cm^2/h$) | Drug absorption rate after 23 hours* ($\mu g/cm^2/h$) |
|---|---|---|---|
| Example 6 | 480.2 | 25.48 | 20.49 |
| Example 7 | 552.5 | 29.38 | 25.16 |
| Example 8 | 665.4 | 34.88 | 25.11 |
| Example 9 | 451.7 | 24.27 | 21.29 |
| Example 10 | 572.9 | 33.36 | 33.36 |
| Comparative Example 4 | 375.7 | 20.71 | 11.04 |
| Comparative Example 5 | 379.2 | 34.35 | 3.89 |

*"Drug absorption rate after 23 hours" refers to a rate calculated by using the cumulative amount of permeated drug after 22 hours and the cumulative amount of permeated drug after 24 hours.

As shown in the results in Tables 7-1 and 7-2, when each cumulative amount of permeated drug after 24 hours from the test start was compared with each other, each patch of Examples 1-5 showed clearly higher value than each patch of Comparative Examples 1 and 2, and each patch of Examples 6-10 showed clearly higher value than each patch of Comparative Examples 4 and 5. Regarding each patch of Comparative Examples 1 and 4, it is believed that the liquid ingredient(s) in the formulation exuded due to the cohesive failure of the adhesive base, the transdermal absorption enhancing effect decreased, and the skin permeability decreased. Each patch of Comparative Examples 2 and 5 showed worse cohesive failure as compared to each patch of Comparative Examples 1 and 4, and the adhesive layer was gel-like. Thus, each patch of Comparative Examples 2 and 5 showed good initial permeability, but did not have sufficient duration of drug absorption due to the exudation of liquid ingredient(s) like each patch of Comparative Examples 1 and 4, and thus showed the rapid decrease in Flux later in the test as shown in FIG. 3 and Table 7-2. On the other hand, each patch of Example 1 and Examples 6-10 could maintain a large amount of liquid ingredients in the formulation, and thus could maintain high permeability without the rapid decrease in Flux. Especially, each patch of Examples 6-10 could maintain high permeability even after 24 hours as shown in Table 7-2. Also, the patch of Example 11 can be subjected to the same test to confirm the high skin permeability and the excellent duration of release of risperidone.

As shown in the above results, the patch of the present invention has high skin permeability and excellent duration of release of risperidone.

INDUSTRIAL APPLICABILITY

According to the present invention, a patch, which shows an excellent drug release property from the formulation and excellent patch physical properties such as having a high cohesive force and causing no exudation of liquid components and no crystal precipitation of the drug etc. during long storage even if liquid components such as carboxylic acids and fatty acid esters are added thereto at a large amount, and being able to be applied to a skin over a long period of time, can be provided.

The invention claimed is:

1. A medical patch comprising an adhesive composition comprising risperidone or a pharmaceutically acceptable salt thereof;
   a carboxylic acid;
   a fatty acid ester; and
   an adhesive,
wherein the adhesive is a star-shaped acrylic block polymer having a star-shaped structure in which at least three chain polymer portions radiate from a sulfur residue of a mercapto group situated at the center, wherein a (meth)acrylic acid alkyl ester structural unit having 7-17 carbon atoms accounts for 30-99.99% by mass of the whole structural units in the star-shaped acrylic block polymer, and at least one of the chain polymer portions has a structural unit having a copolymer structure of polymerizable monomers comprising a (meth)acrylic acid alkyl ester having 7-17 carbon atoms and a polyfunctional monomer; and
   wherein the content of the risperidone or a pharmaceutically acceptable salt thereof is 1-10% by mass, the content of the carboxylic acid is 1-10% by mass, the content of the fatty acid ester is 20-50% by mass, and the content of the adhesive is 40-70% by mass, in the adhesive composition.

2. The medical patch according to claim 1, wherein the content of the polyfunctional monomer relative to the whole structural units of the star-shaped acrylic block polymer is 0.001-1% by mass.

3. The medical patch according to claim 1, wherein the chain polymer comprise a polymeric structure of radical polymerizable monomers.

4. The medical patch according to claim 1, wherein the (meth)acrylic acid alkyl ester having 7-17 carbon atoms is at least one selected from the group consisting of (meth)acrylic acid butyl ester, (meth)acrylic acid t-butyl ester, (meth)acrylic acid pentyl ester, (meth)acrylic acid hexyl ester, (meth)acrylic acid heptyl ester, (meth)acrylic acid octyl ester, (meth)acrylic acid isooctyl ester, (meth)acrylic acid nonyl ester, (meth)acrylic acid isononyl ester, (meth)acrylic acid decyl ester, (meth)acrylic acid undecyl ester, (meth)acrylic acid dodecyl ester, and (meth)acrylic acid 2-ethylhexyl ester.

5. The medical patch according to claim 1, wherein the polyfunctional monomer is at least one bifunctional (meth)acrylate.

6. The medical patch according to claim 1, wherein the polyfunctional monomer is at least one selected from the group consisting of ethylene glycol di(meth)acrylate, diethylene glycol di(meth)acrylate, triethylene glycol di(meth)acrylate, tetraethylene glycol di(meth)acrylate, polyethylene glycol (200) di(meth)acrylate, polyethylene glycol (400) di(meth)acrylate, dipropylene glycol di(meth)acrylate, tripropylene glycol di(meth)acrylate, polypropylene glycol (400) di(meth)acrylate, and 1,6-hexanediol di(meth)acrylate.

7. The medical patch according to claim 1, wherein the chain polymer portion comprises a hydroxy group-containing monomer.

8. The medical patch according to claim 7, wherein the hydroxy group-containing monomer is at least one selected from the group consisting of 2-hydroxyethyl (meth)acrylate, 2-hydroxypropyl (meth)acrylate, and 4-hydroxybutyl (meth)acrylate.

9. The medical patch according to claim 7, wherein a hydroxy value of the star-shaped acrylic block polymer is 5-50.

10. The medical patch according to claim 1, wherein the risperidone or a pharmaceutically acceptable salt thereof is risperidone free base.

11. The medical patch according to claim 1, wherein the carboxylic acid is at least one carboxylic acid having 8 or more carbon atoms.

12. The medical patch according to claim 1, wherein the fatty acid ester is at least one selected from the group consisting of isopropyl myristate, diisopropyl adipate, myristyl myristate, octyldodecyl myristate, isopropyl palmitate, butyl stearate, hexyl laurate, decyl oleate, and diethyl sebacate.

13. The medical patch according to claim 1, which further comprises a surfactant in the adhesive composition.

14. The medical patch according to claim 13, wherein the surfactant is at least one selected from the group consisting of a polyoxyethylene sorbitan fatty acid ester, a polyoxyethylene hydrogenated castor oil, a polyoxyethylene alkyl ether, a polyethylene glycol fatty acid ester, and a sorbitan fatty acid ester.

15. The medical patch according to claim 13, wherein the content of the surfactant in the adhesive composition is 1-10% by mass.

* * * * *